(12) United States Patent
Weigel-Van Aken et al.

(10) Patent No.: US 9,598,468 B2
(45) Date of Patent: Mar. 21, 2017

(54) POLYPEPTIDES AND VECTORS FOR TARGETING HER2/NEU EXPRESSING CELLS AND USES THEREOF

(75) Inventors: Kirsten Ariane Kelley Weigel-Van Aken, Gainesville, FL (US); Mavis Agbandje-McKenna, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 291 days.

(21) Appl. No.: 14/117,871

(22) PCT Filed: May 18, 2012

(86) PCT No.: PCT/US2012/038522
§ 371 (c)(1),
(2), (4) Date: Nov. 15, 2013

(87) PCT Pub. No.: WO2012/159006
PCT Pub. Date: Nov. 22, 2012

(65) Prior Publication Data
US 2014/0093533 A1 Apr. 3, 2014

Related U.S. Application Data

(60) Provisional application No. 61/487,476, filed on May 18, 2011.

(51) Int. Cl.
| | | |
|---|---|---|
| C07K 14/005 | (2006.01) | |
| A61K 47/48 | (2006.01) | |
| C07K 16/32 | (2006.01) | |
| C12N 15/86 | (2006.01) | |
| A61K 9/51 | (2006.01) | |
| A61K 38/00 | (2006.01) | |

(52) U.S. Cl.
CPC ...... *C07K 14/005* (2013.01); *A61K 47/48884* (2013.01); *C07K 16/32* (2013.01); *C12N 15/86* (2013.01); *A61K 9/5184* (2013.01); *A61K 38/00* (2013.01); *C07K 2317/565* (2013.01); *C07K 2319/735* (2013.01); *C07K 2319/74* (2013.01); *C12N 2750/14143* (2013.01); *C12N 2750/14145* (2013.01); *C12N 2750/14322* (2013.01); *C12N 2750/14343* (2013.01); *C12N 2750/14345* (2013.01)

(58) Field of Classification Search
None
See application file for complete search history.

(56) References Cited

U.S. PATENT DOCUMENTS 7,179,785 B2   2/2007  Greene et al.
2009/0215870 A1* 8/2009  Terwilliger et al. ........ 514/44 R
2009/0215879 A1* 8/2009  Diprimio et al. ........... 514/44 R
2009/0263396 A1  10/2009  El-Rifai et al.
2010/0203083 A1  8/2010  Lux et al.

FOREIGN PATENT DOCUMENTS

WO    WO 00/30668    6/2000

OTHER PUBLICATIONS

Fantin et al (Cancer Research 65:6891-6900, 2005).*
Fantin et al, Cancer Research 65:6891-6900, 2005.*
Girod et al (Nature Medicine 5:1052-1056, 1999).*
Shi et al (Human Gene Therapy 12:1697-1711, 2001).*
Grifman et al (Molecular Therapy 3:964-975, 2001).*
Kauffman et al (PNAS 101:11628-11633, 2004).*
Agus, D.B., et al., "Targeting ligand-activated ErbB2 signaling inhibits breast and prostate tumor growth," *Cancer Cell*, 2002, vol. 2, pp. 127-137.
Andreasson, K., et al., "Murine pneumotropic virus chimeric Her2/neu virus-like particles as prophylactic and therapeutic vaccines against Her2/neu expressing tumors," *International Journal of Cancer*, 2009, vol. 124, pp. 150-156, Epub: Oct. 6, 2008.
Berezov, A., et al., "Disabling ErbB Receptors with Rationally Designed Exocyclic Mimetics of Antibodies: Structure-Function Analysis," *Journal of Medicinal Chemistry*, 2001, vol. 44, pp. 2565-2574.
Berezov, A., et al., "Structure-Based Approaches to Inhibition of erbB Receptors with Peptide Mimetics," *Immunologic Research*, 2003, vol. 27, No. 2-3, pp. 303-308.
Brown, K.E., et al., "Erythrocyte P Antigen: Cellular Receptor for B19 Parvovirus," *Science*, 1993, vol. 262, No. 5130, pp. 114-117.
Chau, Y., et al., "Investigation of Targeting Mechanism of New Dextran-Peptide-Methotrexate Conjugates Using Biodistribution Study in Matrix-Metalloproteinase-Overexpressing Tumor Xenograft Model," *Journal of Pharmaceutical Sciences*, 2006, vol. 95, No. 3, pp. 542-551.

(Continued)

*Primary Examiner* — Nicole Kinsey White
(74) *Attorney, Agent, or Firm* — Saliwanchik, Lloyd & Eisenschenk

(57) ABSTRACT

Various aspects of the invention provide for capsids, parvovirus capsids, hybrid parvovirus capsids, parvovirus vectors, hybrid parvovirus vectors, hybrid parvovirus particles and parvovirus particles containing polypeptides in which the sequence YCDGFYACYMDV (SEQ ID NO: 3) has been substituted into the VP2 loop of the B19 capsid protein. Polypeptides in which the sequence YCDGFYACYMDV (SEQ ID NO: 3) has been substituted into the VP2 loop of the B19 capsid protein are also provided (e.g., SEQ ID NO: 2). Other aspects of the invention provides capsids, parvovirus capsids, hybrid parvovirus capsids, parvovirus vectors, hybrid parvovirus vectors, hybrid parvovirus particles and parvovirus particles containing a polypeptide comprising SEQ ID NO: 2. Also provided in various aspects of the invention a pharmaceutical compositions and methods of delivering therapeutic agents and/or reporter peptides/proteins to target cells. Finally, methods of treating diseases characterized by cells expressing HER2/neu receptors are also provided.

Figure 2A:
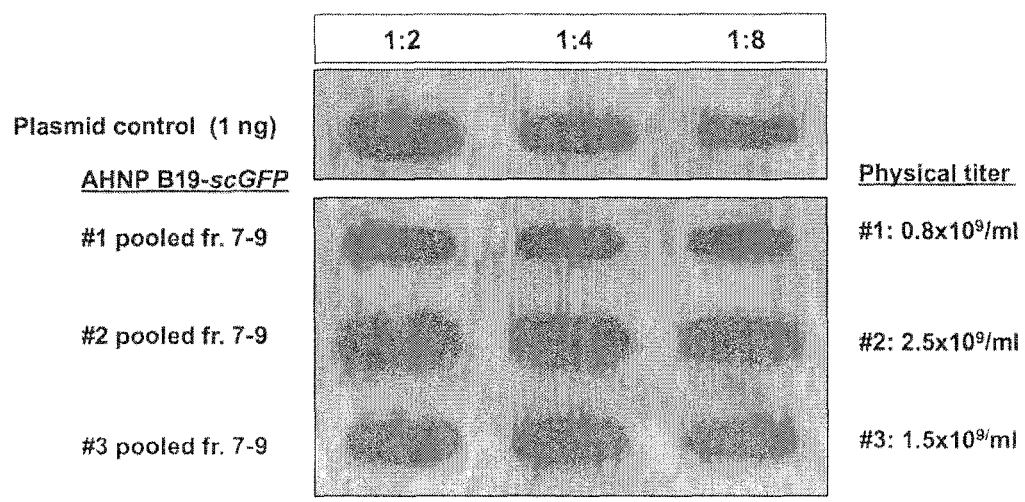

16 Claims, 7 Drawing Sheets
(4 of 7 Drawing Sheet(s) Filed in Color)

(56) References Cited

OTHER PUBLICATIONS

Chipman, P.R., et al., "Cryo-electron microscopy studies of empty capsids of human parvovirus B19 complexed with its cellular receptor," *Proceedings of the National Academy of Sciences USA*, 1996, vol. 93, pp. 7502-7506.
Di Fiore, P.P., et al., "erbB-2 is a Potent Oncogene When Overexpressed in NIH/3T3 Cells," *Science*, 1987, vol. 237, No. 4811, pp. 178-182.
Emsley, P., et al., "*Coot*: model-building tools for molecular graphics," *Acta Crystallographica Section D*, 2004, vol. D60, pp. 2126-2132.
Falcioni, R., et al., "α6β4 and α6β1 Integrins Associate with ErbB-2 in Human Carcinoma Cell Lines," *Experimental Cell Research*, 1997, vol. 236, pp. 76-85.
Harari, D., et al., "Molecular mechanisms underlying ErbB2/HER2 action in breast cancer," *Oncogene*, 2000, vol. 19, pp. 6102-6114.
Horan, T.C., et al., "Description of the cytotoxic effect of a novel drug Abietyl-Isothiocyanate on endometrial cancer cell lines," *Investigational New Drugs*, 2012, vol. 30, No. 4, pp. 1460-1470, Epub Aug. 2011.
Kelly, R.K., et al., "An antibody-cytotoxic conjugate, BIIB015, is a new targeted therapy for Cripto positive tumours," *European Journal of Cancer*, 2011, vol. 47, pp. 1736-1746.
Lockney, D.M., et al., "The *Red clover necrotic mosaic virus* Capsid as a Multifunctional Cell Targeting Plant Viral Nanoparticle," *Bioconjugate Chemistry*, 2011, vol. 22, pp. 67-73.
Lopez-Bueno, A., et al., "Host-Selected Amino Acid Changes at the Sialic Acid Binding Pocket of the Parvovirus Capsid Modulate Cell Binding Affinity and Determine Virulence," *Journal of Virology*, 2006, vol. 80, No. 3, pp. 1563-1573.
Masuda, K., et al., "AHNP-streptavidin: a tetrameric bacterially produced antibody surrogate fusion protein against p184her2/neu," *Oncogene*, 2006, vol. 25, pp. 7740-7746.
Mittendorf, E.A., et al., "Evaluation of the HER2/*neu*-Derived Peptide GP2 for Use in a Peptide-Based Breast Cancer Vaccine Trial," *Cancer*, 2006, vol. 106, No. 11, pp. 2309-2317.
Park B-W., et al., "Rationally designed anti-HER2/neu peptide mimetic disables P185$^{HER2/neu}$ tyrosine," *Nature Biotechnology*, 2000, vol. 18, pp. 194-198.
Ricart, A.D., et al., "Antibody-Drug Conjugates of Calicheamicin Derivative: Gemtuzumab Ozogamicin and Inotuzumab Ozogamicin," *Clinical Cancer Research*, 2011, vol. 17, No. 20, pp. 6417-6427.
Schwede, T., et al., "SWISS-MODEL: an automated protein homology-modeling server," *Nucleic Acids Research*, 2003, vol. 31, No. 13, pp. 3381-3385.
Szabo, R., et al., "Daunomycin-polypeptide conjugates with antitumor activity," *Biochimica et Biophysica Acta*, 2010, vol. 1798, pp. 2209-2216.
Van Rijt, S.H., et al., "Functionalization of Osmium Arene Anticancer Complexes with (Poly)arginine: Effect on Cellular Uptake, Internalization, and Cytotoxicity," *Bioconjugate Chemistry*, 2011, vol. 22, pp. 218-226.
Wang, S., et al., "Novel Targeted System to Deliver Chemotherapeutic Drugs to EphA2-Expressing Cancer Cells," *Journal of Medicinal Chemistry*, 2012, vol. 55, pp. 2427-2436.
Wang, S.E., et al., "Transforming Growth Factor β Induces Clustering of HER2 and Integrins by Activating Src-Focal Adhesion Kinase and Receptor Association to the Cytoskeleton," *Cancer Research*, 2009, vol. 69, pp. 475-482.
Wei, F., et al., "Conjugation of paclitaxel on adeno-associated virus (AAV) nanoparticles for co-delivery of genes and drugs," *European Journal of Pharmaceutical Sciences*, 2012, vol. 46, pp. 167-172.
Weigel-Kelley, K.A., et al., "α5β1 integrin as a cellular coreceptor for human parvovirus B19: requirement of functional activation of β1 integrin for viral entry," *Blood*, 2003, vol. 102, pp. 3927-3933.
Weigel-Kelley, K.A., et al., "Recombinant Human Parvovirus B19 Vectors: Erythrocyte P Antigen is Necessary but Not Sufficient for Successful Transduction of Human Hematopoietic Cells," *Journal of Virology*, 2001, vol. 75, No. 9, pp. 4110-4116.
Weigel-Van Aken, K.A., et al., "Pharmacological Activation of Guanine Nucleotide Exchange Factors for the Small GTPase Rap1 Recruits High-Affinity $β_1$ Integrins as Coreceptors for Parvovirus B19: Improved Ex Vivo Gene Transfer to Human Erythroid Progenitor Cells," *Human Gene Therapy*, 2009, vol. 20, pp. 1665-1678.
Written Opinion in International Application No. PCT/US2012/038522, Nov. 20, 2012, pp. 1-6.
GenBank Accession No. ABP07602.1 "Sequence 113 from U.S. Pat. No. 7,179,785" Apr. 11, 2007.

* cited by examiner

FIG. 1

US 9,598,468 B2

POLYPEPTIDES AND VECTORS FOR TARGETING HER2/*NEU* EXPRESSING CELLS AND USES THEREOF

CROSS-REFERENCE TO RELATED APPLICATION APPLICATIONS

This application is the U.S. national stage application of International Patent Application No. PCT/US2012/038522, filed May 18, 2012, which claims the benefit of U.S. Provisional Application Ser. No. 61/487,476, filed May 18, 2011, the disclosures of which are hereby incorporated by reference in their entirety, including all figures, tables and amino acid or nucleic acid sequences.

The Sequence Listing for this application is labeled "Seq-List-replace.txt" which was created on Aug. 6, 2015 and is 11 KB. The entire contents of the sequence listing is incorporated herein by reference in its entirety.

BACKGROUND OF THE INVENTION

Parvovirus B19 (B19) is a small ssDNA-containing virus that has evolved to be restricted in its replication to erythroid progenitor cells in the human bone marrow. B19 binds to erythroid cells through blood group P antigen or globoside (10). However, it has been demonstrated that P antigen alone is not sufficient for parvovirus B19 infection (54) and that functionally activated α5β1 integrin serves as a coreceptor for internalization into human cells (53). Subsequently, the Ku80 subunit of the DNA double-strand break repair protein Ku, which also functions as an adhesion receptor for fibronectin (31), was reported to also provide coreceptor activity (34).

The human epidermal growth factor receptor 2 (HER2/neu) has been reported to be overexpressed on ~25% of human breast cancers by up to 100-fold the levels present on non-cancerous cells and on ~30-40% of medulloblastomas by up to 5-fold (3, 11, 47). HER2-overexpression has been documented to result in constitutive activation of kinase signaling (57). HER2/neu-positive breast cancers are characterized by poor differentiation, high rates of proliferation, lymph node involvement, a relative resistance to certain types of chemotherapy and poor prognosis (11). About 30% of breast cancer patients present with bone marrow metastases at diagnosis (9). HER2/neu expression is seen in micrometastatic tumors in the bone marrow as well as in primary tumor cells and detection of HER2/neu in circulating tumor cells suggests a stable HER2/neu expression during metastatic spread of breast cancer (21, 35, 39, 50). Thus targeting HER2/neu on breast cancer cells is an attractive therapeutic approach and a humanized anti-HER2 monoclonal antibody (h4D5, trastazumab, Herceptin®) has been developed and tested in clinical trials (17, 25, 40, 42) (38). The mechanisms of Herceptin® action are thought to involve antibody-mediated cytotoxicity (5), blocking of receptor dimerization, removal of HER2/neu from the cell surface by endocytosis, and inhibition of HER2/neu extracellular domain (ECD) shedding by blocking a proteolytic cleavage site, which prevents constitutive tyrosine kinase activation of ECD-less receptors (13, 30) (23, 26, 48). When used as single agent in patients with HER2/neu-positive tumors, however, Herceptin® treatment had relatively high relapse rates (36) and it is currently used with combination chemotherapy (38).

The complementarity-determining regions (CDRs) of antibodies mediate their high-affinity binding and specificity to antigens (4) and peptide analogs of CDRs have been developed for antibodies with known sequences and structures (43). The HER2/neu-binding peptidomimetic (AHNP) was derived from the structure of the CDR-H3 loop of the anti-HER2 antibody rhu 4D5, and was shown to bind to cell surface-expressed HER2/neu, albeit with lower affinity than whole antibodies, and to inhibit HER2/neu kinase activity, modestly down-modulate HER2/neu and sensitize tumor cells to apoptosis when used in conjunction with ionizing radiation or chemotherapeutic agents (7, 37) (28).

Integrins have been suggested to play a cooperative role during oncogenesis, partly attributed to their reciprocal signaling to growth factor receptors (1) (20, 32, 51). Targeted disruption of the β1 integrin chain in a transgenic mouse model of human breast cancer demonstrated a critical role of β1 integrin in initiation and maintenance of mammary tumor growth in vivo (56) and co-clustering of HER2/neu and integrin β1 was demonstrated to be critical for induction of cell migration and survival during breast cancer progression (52). Integrin β1 is known to play an important role in hematopoietic stem and progenitor cell interaction with the bone marrow microenvironment (44), and has recently been identified as one of the adhesion receptors involved in cancer cell survival during genotoxic stresses induced by ionizing radiation and cytotoxic drugs (14, 15, 46).

Equipping viral vectors with the capability to target both HER2/neu and β1 integrins, could allow the delivery of a cytotoxic insult to HER2/neu-positive cancer cells in microenvironments, such as the bone marrow, where pro-survival signals mediated through β1 integrins prevent tumor cell eradication with conventional radiation and chemotherapies. We report here the introduction of the AHNP peptide into the capsid of B19 vectors to replace the endogenous P antigen binding site and demonstrate retargeting of B19 vectors to HER2/neu-positive tumor cells.

BRIEF SUMMARY OF THE INVENTION

Various aspects of the invention provide for capsids, parvovirus capsids, hybrid parvovirus capsids, parvovirus vectors, hybrid parvovirus vectors, hybrid parvovirus particles and parvovirus particles containing polypeptides in which the sequence YCDGFYACYMDV (SEQ ID NO: 3) has been substituted into the loop 4 of the B19 VP2 capsid protein or into loop 8 of a parvovirus VP2 capsid protein. Polypeptides in which the sequence YCDGFYACYMDV (SEQ ID NO: 3) has been substituted into the loop 4 of the B19 VP2 capsid protein are also provided (e.g., SEQ ID NO: 2). Other aspects of the invention provides capsids, parvovirus capsids, hybrid parvovirus capsids, parvovirus vectors, hybrid parvovirus vectors, hybrid parvovirus particles and parvovirus particles containing a polypeptide comprising SEQ ID NO: 2. Also provided in various aspects of the invention are pharmaceutical compositions and methods of delivering therapeutic agents, DNA/RNA/peptides/proteins and/or reporter DNA/RNA/peptides/proteins to target cells. Finally, methods of treating diseases characterized by cells expressing HER2/neu receptors are also provided.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
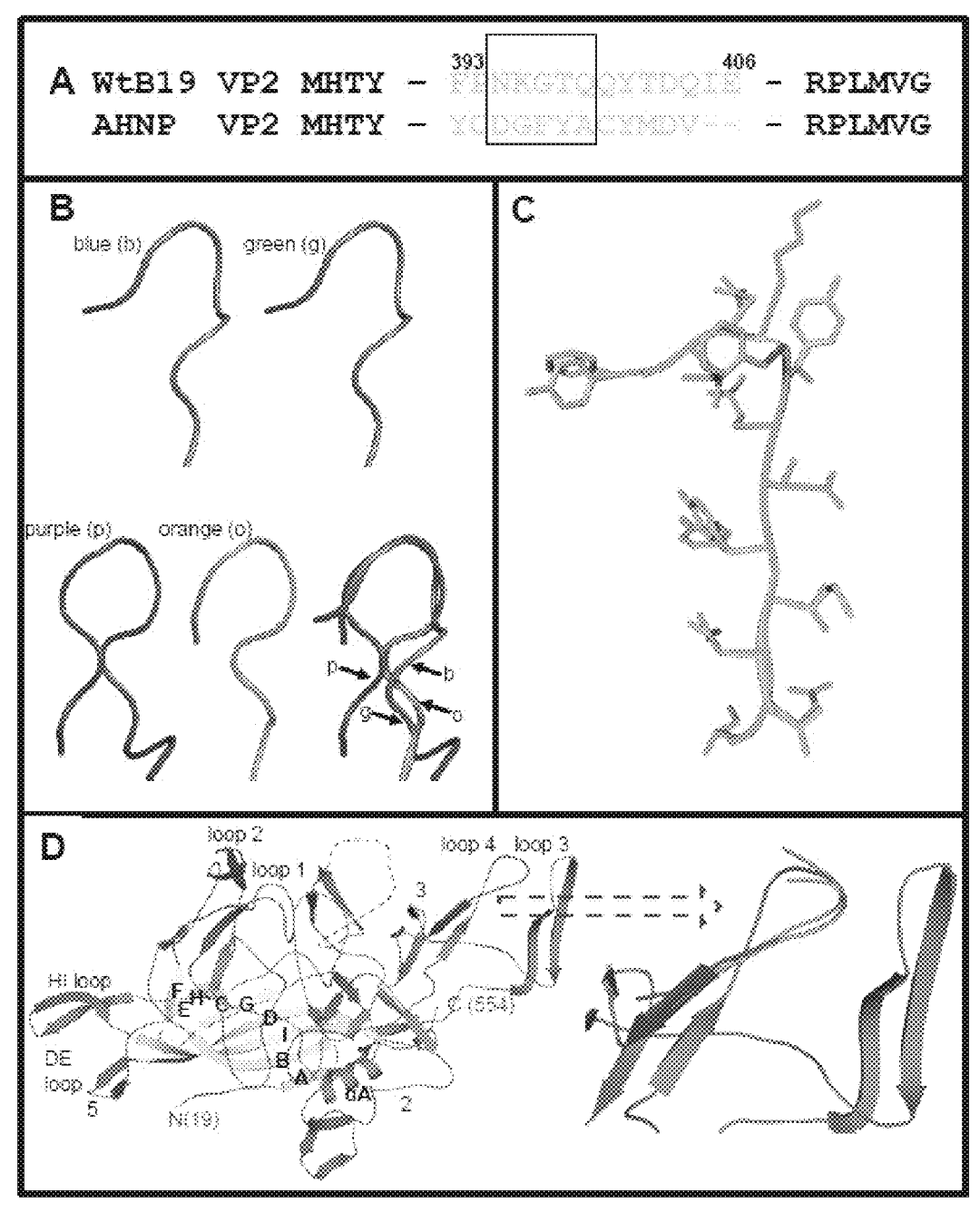

FIGS. 1A-1D. Structural grafting of the AHNP peptide onto the B19 VP2 monomer. (A) A sequence alignment of the AHNP peptide sequence with the sequence of B19 VP2 region containing the proposed P antigen binding site amino acids. The residues shown in green (SEQ ID NO: 5) were replaced with those shown in orange (SEQ ID NO: 3) in the chimeric AHNP-B19 VP2. (B) A superimposition of the Cα trace of the loop region replaced for wt B19 (blue), the SWISS-generated model AHNP peptide loop model (green), the rhu 4D5 CDR-H3 loop structure on which the AHNP peptide design was based (purple), the interactive AHNP peptide loop model generated in the Coot program (orange) (left hand side) and the same loops with the amino acid positions of the DGFYA peptide important for receptor binding superimposed (right hand side). (C) Superimposition of the AHNP peptide loop model generated in the Coot program (orange) and the SWISS MODEL generated AHNP peptide loop model (green). (D) A ribbon diagram showing the secondary structure of the B19 VP2 monomer with the substituted region in loop 4 shown for wt (blue). A close-up view indicated by the arrow of the wt B19 region in loop 4 (blue) shows the AHNP peptide loop model generated in the Coot program (orange) and the SWISS MODEL generated AHNP peptide loop model (green). The N- and C-terminal regions observed in the crystal structure, with the secondary structure elements and loop regions, and the approximate icosahedral 2-, 3-, and 5-fold axes are labeled. The stretch of amino acids that were disordered in the structure (amino acids 301-313) is indicated with the dashed lines.

FIGS. 2A-2C. Analysis of B19-scGFP and AHNP-B19-scGFP fractions from iodixanol gradients. (A) Pooled and concentrated samples from fractions 7-9 of three separate iodixanol gradients (corresponding to the 40% phase) were analyzed by slot blot for presence of encapsidated genomes. Samples and control plasmids were loaded at 2-fold dilutions. (B) Western blot analysis of fractions 6-18 of B19-scGFP (top panel) and AHNP-scGFP vector preparations (bottom panel) using anti-B19 VP2 antibodies. Purified B19-scGFP virions were included as control (lane C); B19 VP2, parvovirus B19 capsid protein 2 (58 kDa); *, VP2 break-down product. (C) Infectious assay. Phase contrast (Phase) and fluorescent microscopy (GFP) images of murine MMTV-HER2/neu-transgenic mammary tumor cells exposed to fractions 7-9, 10-12, and 13-15 of iodixanol gradients. Images were acquired 24 h post infection.

FIG. 3. B19-scGFP and AHNP-B19-scGFP-mediated transgene expression in murine MMTV-HER2/neu-transgenic mammary tumor cells. Phase contrast and fluorescent microscopy images of murine MMTV-HER2/neu-transgenic mammary tumor cells exposed to B19-scGFP (top left panels: GFP left, phase right) and AHNP-B19-scGFP vectors (top right panels: GFP left, phase right) 24 h post infection demonstrated significantly higher GFP transgene expression in AHNP-scGFP transduced cells (bottom).

FIGS. 4A-4C. Dependence of AHNP-B19 infection on HER2 kinase activity. (A) Western blot detection of phosphorylated tyrosine 1248 ($^{P1248}$-HER2) and total HER2 in cell extracts from MMTV-HER2/neu mammary tumor cells in the absence and presence of peptides derived from the activation loop of the kinase domain (p1) or the transmembrane region (p2) of the HER2/neu receptor. (B) Phase contrast and fluorescent microscopy images of murine MMTV-HER2/neu-transgenic mammary tumor cells exposed to B19-scGFP (left panels) and AHNP-B19-scGFP vectors (right panels) in the absence and presence of inhibitory β1 integrin antibodies (second panels); peptides derived from the activation loop of the HER2/neu kinase domain (third panels). For inhibition of P antigen binding, virions were pre-incubated with recombinant P antigen for 1.5 h on ice prior to addition to cells (fourth panels). (C) Quantitative analyses of B19-scGFP and AHNP-B19-scGFP transduction efficiencies. Images from five visual fields were analyzed quantitatively by ImageJ analysis software. Transgene expression was assessed as total area of green fluorescence ($pixel^2$ per visual field) and mean±SD are depicted. Students t test was used to compare the groups. *p≤0.05; **p≤0.001.

FIG. 5. B19-scGFP and AHNP-B19-scGFP-mediated transgene expression in Daoy medulloblastoma cells. Quantitative analyses of B19-scGFP and AHNP-B19-scGFP transduction efficiencies. Images from three to five visual fields were analyzed quantitatively by ImageJ analysis software. Transgene expression was assessed as total area of green fluorescence ($pixel^2$ per visual field) and mean±SD are depicted. Students t test was used to compare the groups. *p≤0.05.

DETAILED DISCLOSURE OF THE INVENTION

In a first aspect of the invention, a polypeptide in which the sequence YCDGFYACYMDV (SEQ ID NO: 3) has been substituted into loop 4 of the B19 VP2 capsid protein is provided. In certain embodiments, amino acid positions 393-406 of SEQ ID NO: 1 (VP2 loop 4 residues 393-FPNKGTQQYTDQIE-406 of SEQ ID NO: 1) are substituted with YCDGFYACYMDV (SEQ ID NO: 3) (see, for example, SEQ ID NO: 2). Other aspects of the invention provide for the substitution of SEQ ID NO: 3 into loop 8 of a parvovirus VP2 capsid protein (for variable region/loop annotation please see Ng R. JVI 84: 12945-57, 2010). Another aspect of the invention provides capsids, parvovirus capsids, hybrid parvovirus capsids, parvovirus vectors, hybrid parvovirus vectors, hybrid parvovirus particles and parvovirus particles containing polypeptides in which the sequence YCDGFYACYMDV (SEQ ID NO: 3) has been substituted into the VP2 loop of the B19 capsid protein or into loop 8 of a parvovirus VP2 capsid protein (for variable region/loop annotation please see Ng R. JVI 84: 12945-57, 2010). Yet another aspect of the invention provides capsids, parvovirus capsids, hybrid parvovirus capsids, parvovirus vectors, hybrid parvovirus vectors, hybrid parvovirus particles and parvovirus particles containing a polypeptide comprising SEQ ID NO: 2.

One aspect of the present invention provides parvovirus vectors for the in vitro and in vivo delivery of nucleic acids to cells. Another aspect of the invention provides novel capsid structures for use in the delivery of compounds and other therapeutic agents to cells expressing the HER2/neu receptor by conjugating cytotoxic drugs, including but not limited to, intercalators (including enediynes (59) and metallic intercalators (60)), taxanes (61), maytansine (62), methotrexate (63), anthracyclines (e.g. daunomycin) (64), and isothiocyanates (65) to the outside (66) and/or inside of the HER2-AHNP B19 capsid, and/or infusing respective drugs into HER2-AHNP B19 capsids (67). The parvovirus vectors of the present invention can utilize properties associated with gene delivery by adeno-associated virus (AAV) vectors while specifically targeting cell populations expressing the HER2/neu receptor.

The term "parvovirus" as used herein encompasses all parvoviruses, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, mouse minute virus, bovine parvovirus, canine parvovirus, chicken parvovirus, feline panleukopenia virus, feline parvovirus, goose parvovirus, and B19 virus. Other autonomous parvoviruses are known to those skilled in the art.

The genus Dependovirus contains the adeno-associated viruses (AAV), including but not limited to, AAV type 1, AAV type 2, AAV type 3, AAV type 4, AAV type 5, AAV type 6, AAV type 7, AAV type 8, AAV type 9, AAV type rh32.33, avian AAV, bovine AAV, canine AAV, equine AAV, and ovine AAV. In certain embodiments, parvovirus particles, capsids and genomes of the present invention can be from the B19 parvovirus.

The term "tropism" refers to entry of the virus into the cell. In certain aspects of the invention, expression of sequences carried by the viral genome in the cell, e.g., for a recombinant virus, expression of the heterologous nucleotide sequences(s), follows entry of the virus into the cell. Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of parvovirus and AAV, gene expression from the viral genome may be from a stably integrated provirus, from a non-integrated episome, as well as any other form in which the virus may take within the cell.

The parvovirus vectors of the present invention are useful for the delivery of nucleic acids to cells both in vitro and in vivo. In particular, the vectors described herein can be used to deliver or transfer nucleic acids to mammalian cells expressing a HER2/neu receptor. Nucleic acids of interest include nucleic acids encoding peptides and proteins that are, preferably, therapeutic (e.g., for medical or veterinary use). Alternatively, reporter peptides/proteins, such as green fluorescent protein or the like, can also be delivered to a target cell expressing the HER2/neu receptor. In certain embodiments, RNA molecules including but not limited to siRNA, shRNA or antisense RNA molecules can be delivered using parvovirus vectors disclosed herein.

A "therapeutic agent" is a peptide or protein or a nucleic acid or a cytotoxic drug that can be used to induce cell death or inhibit metastasis in a HER2/neu receptor expressing cell (e.g., a breast cancer cell). Non-limiting examples of such proteins or peptides are encoded by suicide genes, tumor suppressor genes or genes encoding cytokines. Suicide genes can be defined as genes that are able to convert a nontoxic prodrug into a toxic drug and non-limiting examples of such genes are those encoding Herpes simplex virus thymidine kinase (HSV-tk)/acyclovir (ACV) or ganciclovir (GCV), and the bacterial or fungal cytosine deaminase (CD)/5-florocytosine (5-FC). Non-limiting examples of tumor suppressor genes include p53. p21WAF1/CIP1 (p21), p16INK4a (p16), p18INK4c (p18), p27KIP2 (p27), Rb, Wt-1, NF1, VHL, APC, and the like. Exemplary cytokines that can be delivered using the vectors disclosed herein include are IL-1, 2, 4, 5, and 12, IFN-α, β, and γ, GM-CSF and TNF.

As discussed above, the vectors disclosed herein can also be used to deliver chemical compounds to a cell expressing a HER2/neu receptor. Chemical compounds with cytotoxic properties are known in the art and include, but are not limited to, intercalators (including enediynes (59) and metallic intercalators (60), taxanes (61), maytansine (62), methotrexate (63), anthracyclines (e.g. daunomycin) (64), and isothiocyanates (65) and can be attached to the outside (66) and/or "packaged"/conjugated/infused inside of the HER2-AHNP B19 capsid (67).

The term "packaged" refers to the process by which recombinant viral DNA is inserted into the parvoviral capsid by a self-assembly process within the host cell (e.g., HEK293 cell) used for viral vector generation.

As discussed above, the vectors disclosed herein can also be used to deliver a heterologous nucleic acid sequence encoding a reporter peptide/protein to a cell expressing a HER2/neu receptor. Non-limiting examples of such reporter proteins include may encode a reporter peptide or protein (e.g., an enzyme). Reporter proteins are known in the art and include, but are not limited to, Green Fluorescent Protein, β-galactosidase, alkaline phosphatase, chloramphenicol acetyltransferase, and the like. Cytotoxic drugs delivered by the AHNP-B19 vector to HER2-expressing cells include, but are not limited to, intercalators, taxanes, maytansine, methotrexate, anthracyclines, and isothiocyanates conjugated to either the outside of the AHNP-B19 vector capsid or conjugated/packaged inside the AHNP-B19 vector capsid.

Except as otherwise indicated, standard methods known to those skilled in the art may be used for the construction of parvovirus genomes and particles suitable for the delivery of therapeutic agents to a HER2/neu receptor expressing cell.

Yet another aspect of the invention provides for a "hybrid parvovirus" vector for delivery of nucleic acids or other molecules to cells. The term "hybrid parvovirus" is used to denote an AAV genome encapsidated within a different parvovirus capsid (for example a B19 capsid). In particular preferred embodiments the parvovirus capsid is a B19 capsid as described herein. For example, a recombinant AAV type 1, 2, 3, 4, 5, 6, 7, 8, 9, 10, rh32.33 or B19 genome may be encapsidated within an B19 capsid containing a sequence that targets the virus to HER2/neu receptor expressing cells. In embodiments, the hybrid parvovirus particle contains a rAAV genome that carries at least one heterologous nucleic acid sequence to be delivered to a cell. Those skilled in the art will appreciate that the rAAV genome can encode more than one heterologous nucleic acid sequence (e.g., two, three or more heterologous nucleic acid sequences) and is, in general, only limited by the packaging capacity of the virus capsid. Heterologous nucleic acid sequence(s) for expressing within a target cell (e.g., a HER2/neu receptor expressing cell) are as described above and can be regulated with promoters/enhancers that are native or which may be inducible.

Any method of introducing a vector, as disclosed herein, into a target cell can be used, including but not limited to, electroporation, calcium phosphate precipitation, microinjection, cationic or anionic liposomes, and liposomes in combination with a nuclear localization signal. However, the parvovirus and hybrid parvovirus vectors disclosed herein can also be introduced into a target cell using the HER2/neu receptor.

Another aspect of the invention provides hybrid parvovirus vectors that contain chimeric capsids and/or capsids that have been modified by insertion of an amino acid sequence(s) into the capsid that confers the ability of the vectors to bind to the HER2/neu receptor (e.g., substitution of VP2 loop residues 393-FPNKGTQQYTDQIE-406 (SEQ ID NO: 5), containing with the sequence of the AHNP peptide, YCDGFYACYMDV (SEQ ID NO: 3) into the capsid polypeptide of the B19 virus).

The methods of the present invention provide a means for delivering heterologous nucleic acid sequences and/or other compounds into cells expressing a HER2/neu receptor. The vectors and other reagents, methods and pharmaceutical formulations of the present invention are additionally useful in a method of delivering a therapeutic agent to a subject in a method of treatment of diseases, including, but not limited to breast cancer, medulloblastoma, lung cancer (e.g., non-small cell lung cancer), uterine cancer (e.g., uterine serous endometrial carcinoma), stomach cancer and ovarian cancer. Therapeutic agents suitable for delivery to a subject in need of treatment are discussed above.

For the purposes of this invention, the term "subject" refers to mammals, such as humans, mice, rats, apes, chimpanzees, orangutans, monkey, dog, cat, guinea pig, hamster, rabbits, ferrets, cows, horses, goats and sheep and in which disease causing cells (e.g., cancer cells) expressing HER2/neu receptors are found. The disease causing cells can arise naturally in the subject (i.e., by the development of, for example, breast cancer in a human) or be introduced into the mammal via injection of cancer cells or cancer cell lines expressing HER2/neu receptors (i.e., in animal models of disease).

In other aspects of the invention, a pharmaceutical composition comprising a virus particle, a polypeptide, a parvovirus vector or a hybrid parvovirus, as disclosed herein, in a pharmaceutically-acceptable carrier, adjuvant or diluent is provided. For injection, the carrier will typically be a liquid. Pharmaceutically acceptable carriers, adjuvants and diluents are well-known to those skilled in the art and can contain the additives usual for injection solutions, such as stabilizing agents, salts or saline, and/or buffers. Exemplary modes of administration include oral, rectal, transmucosal, topical, transdermal, inhalation, parenteral (e.g., intravenous, subcutaneous, intradermal, intramuscular, and intraarticular) administration. Injectables can be prepared in conventional forms, either as liquid solutions or suspensions, solid forms suitable for solution or suspension in liquid prior to injection, or as emulsions. Alternatively, one may administer the virus in a local rather than systemic manner, for example, in a depot or sustained-release formulation.

In certain embodiments of the invention, more than one administration (e.g., two, three, four, or more administrations) may be employed to achieve delivery of therapeutic agents to target cells expressing a HER2/neu receptor. As would be apparent to those skilled in the art, the parvovirus and hybrid parvovirus vectors provided herein can be administered alone or in combination with standard treatment protocols/regimens for a particular cancer characterized by expression of HER2/neu receptors (e.g., breast cancer). Furthermore, certain embodiments of the invention contemplate the administration of the parvovirus and hybrid parvovirus vectors provided herein to a subject after the completion of a treatment regimen for a cancer characterized by expression of HER2/neu receptors (e.g., breast cancer). In these embodiments, the parvovirus and hybrid parvovirus vectors provided herein can be administered to a subject up to 5 years (or more) after the completion of a treatment regimen for a cancer characterized by expression of HER2/neu receptors (e.g., breast cancer).

Thus, the following non-limiting embodiments are provided:

1. An isolated polypeptide in which:
a) the sequence YCDGFYACYMDV (SEQ ID NO: 3) has been substituted into loop 8 of a parvovirus VP2 capsid protein (for variable region/loop annotation please see Ng R. JVI 84: 12945-57, 2010); or
b) the sequence YCDGFYACYMDV (SEQ ID NO: 3) has been substituted into loop 4 of a parvovirus B19 VP2 capsid protein for the P antigen binding site.

2. The isolated polypeptide according to embodiment 1, wherein said polypeptide comprises SEQ ID NO: 2.

3. A capsid comprising a polypeptide according to any one of embodiments 1 or 2.

4. A parvovirus or hybrid parvovirus particle comprising a polypeptide according to any one of embodiments 1 or 2.

5. A parvovirus or hybrid parvovirus vector comprising nucleic acid encoding one or more therapeutic agent or one or more reporter peptide or protein, said parvovirus vector comprising a capsid comprising a polypeptide according to any one of embodiments 1 or 2.

6. A parvovirus or hybrid parvovirus vector comprising a cytotoxic compound/drug (e.g., including, but not limited to, chemotherapeutics such as intercalators, taxanes, maytansine, methotrexate, anthracyclines and isothiocyanates) packaged/conjugated/infused in and/or associated with said parvovirus vector comprising a caspid comprising a polypeptide according to any one of embodiments 1 or 2.

7. The parvovirus or hybrid parvovirus vector according to embodiment 5, wherein said one or more therapeutic agent is a suicide gene, a tumor suppressor gene or a gene encoding a cytokine.

8. The parvovirus or hybrid parvovirus vector according to embodiment 7, wherein said nucleic acid encodes one or more RNA molecule (e.g., including, but not limited to antisense RNA, siRNA or shRNA) and/or one or more of the following polypeptides: Herpes simplex virus thymidine kinase (HSV-tk)/acyclovir (ACV), ganciclovir (GCV), bacterial or fungal cytosine deaminase (CD)/5-florocytosine (5-FC), p53, p21WAF1/CIP1 (p21), p16INK4a (p16), p18INK4c (p18), p27KIP2 (p27), Rb, Wt-1, NF1, VHL, APC, IL-1, IL-2, IL-4, IL-5, IL-12, IFN-α, IFN-β, GM-CSF or TNF.

9. The parvovirus or hybrid parvovirus vector according to embodiment 6, wherein said one or more therapeutic agent is a cytotoxic drug, including but not limited to DNA intercalators, taxanes, maytansine, methotrexate, anthracyclines and isothiocyanates.

10. The parvovirus or hybrid parvovirus vector according to embodiment 5, wherein said one or more reporter peptide/protein is Green Fluorescent Protein, β-galactosidase, alkaline phosphatase or chloramphenicol acetyltransferase.

11. A pharmaceutical composition comprising a pharmaceutically-acceptable carrier, adjuvant or diluent and a polypeptide, parvovirus capsid, parvovirus particle or parvovirus vector according to any one of embodiments 1-10.

12. A method of delivering a nucleic acid, therapeutic agent, reporter peptide or cytotoxic drug to a cell expressing one or more HER2/neu receptor comprising contacting said cell expressing one or more HER2/neu receptor with a parvovirus vector or a hybrid parvovirus vector according to any one of embodiments 5-9, said parvovirus or hybrid parvovirus vector optionally being contained in a pharmaceutical composition.

13. A method of treating a cancer characterized by expression of HER2/neu receptors on a cell surface comprising the administration of a parvovirus vector or a hybrid parvovirus vector according to any one of embodiments 5-9 to a subject having a cancer characterized by expression of HER2/neu receptors on a cell surface, said parvovirus or hybrid parvovirus vector optionally being contained in a pharmaceutical composition.

14. The method according to embodiment 13, wherein said cancer is selected from breast cancer, medullablastoma, lung cancer, non-small cell lung cancer, uterine cancer, uterine serous endometrial carcinoma, stomach cancer or ovarian cancer.

15. The method according to embodiment 13 or 14, wherein said subject is a human.

16. The method according to embodiment 15, wherein said parvovirus vector or a hybrid parvovirus vector is administered alone or in combination with a treatment regimen for said cancer.

17. The method according to embodiment 15, wherein said parvovirus vector or a hybrid parvovirus vector is administered to a subject after a treatment regimen for a cancer has been completed.

18. The method according to embodiment 16 or 17, wherein said cancer is breast cancer.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLES

Material and Methods
Structural Modeling of the Chimeric AHNP-B19 VP2.

The crystal structure of the B19 capsid VP2 (PDB accession No. 1S58) was used as a template onto which the HER2/neu peptide, AHNP, was inserted using two strategies: (I) interactive substitution mutation of VP2 loop residues 393-FPNKGTQQYTDQIE-406 (SEQ ID NO: 5), containing the proposed P-antigen binding site footprint, 399-QQYTDQIE-406 (SEQ ID NO: 6) (12), with the sequence of the AHNP peptide, YCDGFYACYMDV (SEQ ID NO: 3), in the program Coot (18) and (II) automatic 3D model generation using the SWISS-MODEL online molecular modeling program, SMR-Pipeline (45). In the first approach, the coordinates of the anti-HER2/neu antibody rhu 4D5 CDR-H3 loop amino acids RWGGDGFYAMDV (SEQ ID NO: 4), on which the AHNP-peptide design is based, was extracted from the crystal structure of the antibody (PDB accession No. 1FVD) and compared to the structure of the B19 VP2 loop containing the P antigen binding site to identify the optimal amino acids to be substituted with the AHNP peptide to maintain the structural conformation of the DGFYA (SEQ ID NO: 7) sequence essential for the HER2/neu receptor recognition and eliminate the P antigen binding site. Sequence comparison of the B19 VP2 loop amino acids with the AHNP peptide and rhu 4D5 CDR-H3 loop sequences as well as the structural comparison to the rhu 4D5 CDR-H3 loop structure (by superimposition) identified the stretch of amino acids from 393-406 for the substitution. B19 VP2 amino acids 393-404 were interactively substituted with the AHNP peptide amino acids, residues 405 and 406 were deleted, the Cα position of the tyrosine 398 and alanine 399 were rotated to be the same as the equivalent residues in the rhu 4D5 crystal structure, and the model geometry was regularized (18). In the second approach, B19 VP2 amino acids 393-406 were deleted from the sequence (NCBI Accession No. M13178), replaced with those of the AHNP peptide amino acids (YCDGFYACYMDV, SEQ ID NO: 3), and submitted to the SMR-Pipeline along with the coordinates for the B19 VP2 crystal structure supplied as the user identified template for automated model building (45). The final total energy for the model generated was −7919.273 KJ/mol. The main chain conformation of the energy minimized model generated from this second approach was essentially identical to that obtained by the interactive mutation in Coot with the exception of the Cα positions for amino acid positions 398 and 399 which were adjusted as described above.

Cells, Plasmids, Peptides.

Murine mammary gland tumor cells derived from MMTV-HER2/neu transgenic mice were a kind gift from. Dr. Hao-Yuan Yiang (Indiana University) and were maintained in Iscove's Dulbecco's medium (IMDM) supplemented with 10% fetal calf serum and 1% penicillin-streptomycin (Sigma-Aldrich, St. Louis, Mo.). Cells were subcultured every 3 days to avoid tumor nodule formation. Replacement of amino acids 393 to 406 of B19 VP2 by an anti-HER2/neu peptide was performed by PCR-based mutagenesis and the resulting AHNP-B19 plasmid was confirmed by sequencing. Peptides derived from HER2 were purchased from CHI Scientific (Maynard, Mass.).

Recombinant B19 Vector Generation and Purification.

Recombinant wt-VP2 and AHNP-VP2 B19 vectors containing self-complementary AAV2 genomes encoding a chicken β-actin promoter-driven green fluorescent protein (B19-scGFP and AHNP-B19-scGFP) were generated by triple plasmid transfection of HEK293 cells as previously described (54). Viral vectors were purified using discontinuous iodixanol gradient centrifugation. One milliliter fractions were collected from the bottom of the tube and dialyzed against phosphate buffered saline (PBS) overnight at 4° C.

Western Blot Analysis.

The localization of assembled B19 capsids within the iodixanol gradient was evaluated by SDS-PAGE and western blot using an anti-B19 VP2 antibody (Millipore, Billerica, Mass.). Analysis of the phosphorylation status of HER2/neu receptors on MMTV-HER2/neu cells following exposure to either HER2 kinase domain (p1)- or HER2/neu transmembrane domain (p2)-derived peptides was evaluated using antibodies specific for phosphorylated tyrosine 1248 ($^{P1248}$HER2) and antibodies detecting total levels of HER2/neu (CHI Scientific, Maynard, Mass.).

Infectious Assays.

Fractions containing the 60/40%, 25% and 15% phases of the iodixanol gradient were pooled and concentrated using Amicon Ultra-4 centrifugal filter devices (100,000 MWCO, Millipore, Billerica, Mass.). Physical genome titers were determined using slot blot analysis as previously described (54). The presence of infectious viral particles was evaluated in HER2/neu-overexpressing MMTV-HER2/neu murine tumor cells plated in 12-well plates and exposed to 100 μl of dialyzed and pooled iodixanol fractions for 2 h at 37° C. in serum-free medium.

Inhibitor Studies.

MMTV-HER2/neu cells were plated in 12-well plates and exposed to 10 μg/ml of P4C10 monoclonal antibodies that inhibit β1 integrin function by stabilizing its inactive conformation (Millipore, Billerica, Mass.), or 1 μg/ml of HER2 peptides derived from either the kinase domain (p1) or the transmembrane domain (p2) of the receptor (CHI Scientific, Maynard, Mass.) for 30 min prior to infection with B19-scGFP- or AHNP-B19-scGFP vectors at MOI 10 for 2 h at 37 C in serum-free medium. For P antigen binding inhibition, viral vectors were pre-incubated with 10 μg of globoside (globotetraosylceramide, Sigma-Aldrich, St. Louis, Mo.) for 90 min on ice before addition to the cells. Fluorescent microscopy and phase contrast images were collected on a Zeiss Fluorescent Microscope 24 h after infection. Images from three to five visual fields were analyzed quantitatively by ImageJ analysis software (National Institutes of Health, Bethesda, Md.). Transgene expression was assessed as total area of green fluorescence (pixels squared per visual field) (mean±SD). P values were calculated by Student t test.

Results

Structural Modeling Shows that the Putative P Antigen Binding Site on B19 VP2 can be Replaced with the AHNP Peptidomimetic.

In order to generate parvovirus B19 vectors that target cancer cells and not erythroid progenitor cells, the P antigen binding epitope on B19 capsids (12) was replaced with an alternative peptide, AHNP, that promotes binding to the cell surface receptor HER2/neu, which is highly expressed on a subgroup of breast cancers and medulloblastomas (3, 11), based on structural modeling. A model of the B19 VP2 was built in which residues 393-406 in loop 4, carrying the putative P antigen binding site footprint (aa 393-406), were replaced with the 12 amino acid sequence of AHNP (FIGS. 1A and 1C). This required the deletion of residues 405 and 406 to ensure that all the residues proposed as the P antigen binding site were eliminated. Comparison of the VP2 model resulting from the two different approaches (as described in Materials and Methods) to the crystal structure of the CDR-H3 loop of the rhu 4D5 (FIG. 1B, purple) on which the AHNP peptide was based showed structural superimposition of residues DGF, thus the conformation of residues Y and A were adjusted to be the same as those in the rhu 4D5 structure (FIGS. 1B and C, green=SWISS MODEL generated AHNP loop; orange=AHNP generated by interactive mutation in the Coot program based on a superimposition of the B19 P antigen loop (blue) and the rhu 4D5 crystal structure (purple)). These adjustments were made without affecting conformation of the main chain for the remainder of the residues in this loop in the wild-type B19 VP2 structure. The modeled loop is easily accommodated within the VP2 monomer structure (FIG. 1C). Based on the structural model, 14 amino acids of B19 VP2 were replaced with the 12 amino acid AHNP peptide using PCR-based mutagenesis and sequence confirmed by DNA sequencing.

Packaging and Purification of Recombinant wt and AHNP-B19-scGFP Virions.

Figure 2B:
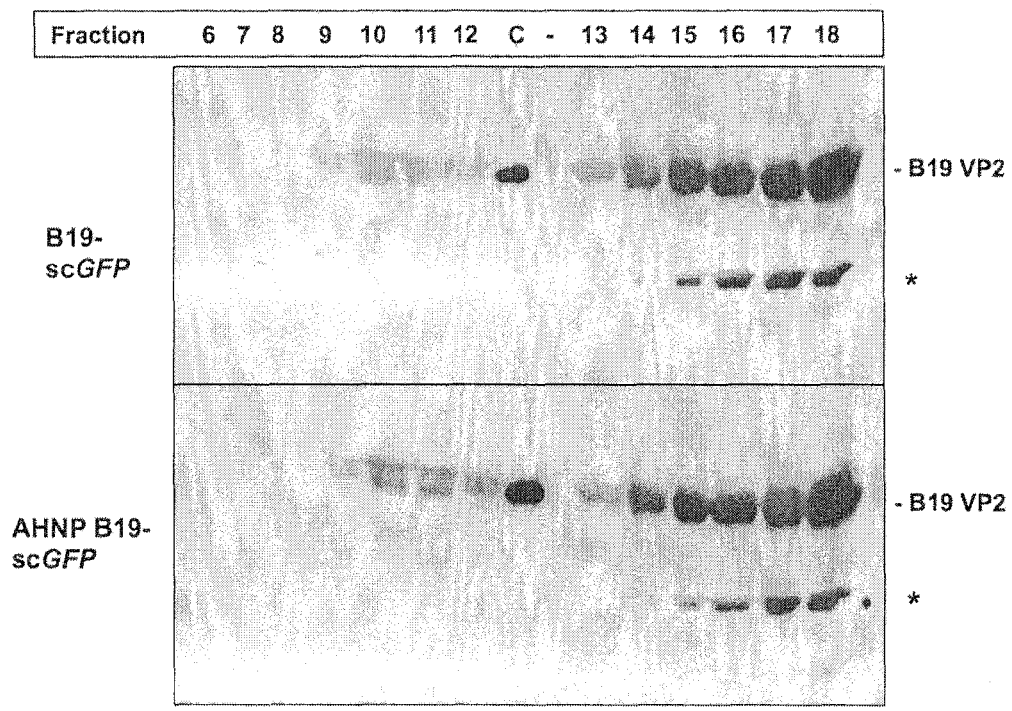
Figure 2C:
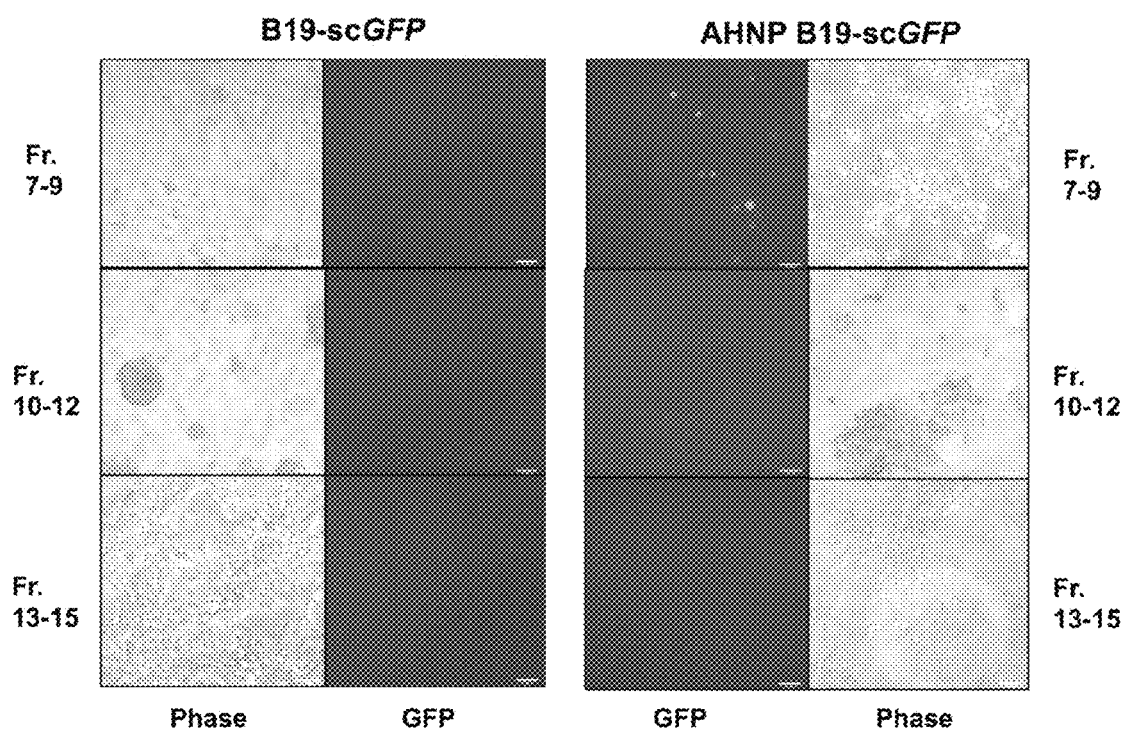

Self-complementary AAV2 genomes containing a chicken β-actin promoter-driven green fluorescent protein gene were packaged into capsids comprised of either wt B19 VP2 (B19-scGFP) or AHNP-VP2 proteins (AHNP-B19-scGFP) as reported previously (53, 54). Virus preparations were purified on discontinuous iodixanol gradients and physical titers were determined by slot blot analysis following DNAse treatment. Physical titers of AHNP-B19-scGFP vectors were comparable to titers of B19-scGFP vectors (~1-$2\times10^9$/ml, (54) (FIG. 2A). SDS-PAGE electrophoresis and western blot analysis of fractions 7-18 of the gradients revealed a single band at 58 kDa representative of B19 VP2 (FIG. 2B, lane C purified virus control) and additional bands of lower molecular weight (FIG. 2B, lanes 14-18), representing break-down products of B19 VP2. The presence of DNA-containing particles in gradient fractions was determined by infectious assays. Murine mammary gland tumor cells from mice transgenic for a mouse mammary tumor virus-LTR driven HER2/neu gene (MMTV-LTR HER2/neu-transgenic mice) (33) were incubated with pooled, dialyzed and concentrated fractions from the lower (fractions 7-9), middle (fractions 10-12) and upper (fractions 13-15) sections of the iodixanol gradient. Fluorescent microscopy images of cells 24 h after infection revealed GFP-positive cells only in cells exposed to fractions 7-9 of the AHNP-B19-scGFP gradient (FIG. 2C, upper panel on the right) and not cells exposed to B19-scGFP fractions (FIG. 2C, panels on the left) or AHNP-B19-scGFP fractions 10-15 (FIG. 2C, middle and lower panel on the right). These results indicated that DNA-containing infectious AHNP-B19-scGFP particles were present in the 40% iodixanol phase of the gradient (fractions 7-9) and B19 VP2 signals detected in fractions 10-18 represented either empty particles (likely in fractions 10-12) or free VP2 capsid proteins (fractions 12 and above) (FIG. 2B). Based on these results, the partial replacement of loop 4 of B19 VP2 by an AHNP peptide did not affect assembly or packaging of mutant vectors.

Efficient Transduction of HER2/neu Expressing Cells with AHNP-B19-scGFP Vectors.

Figure 3:
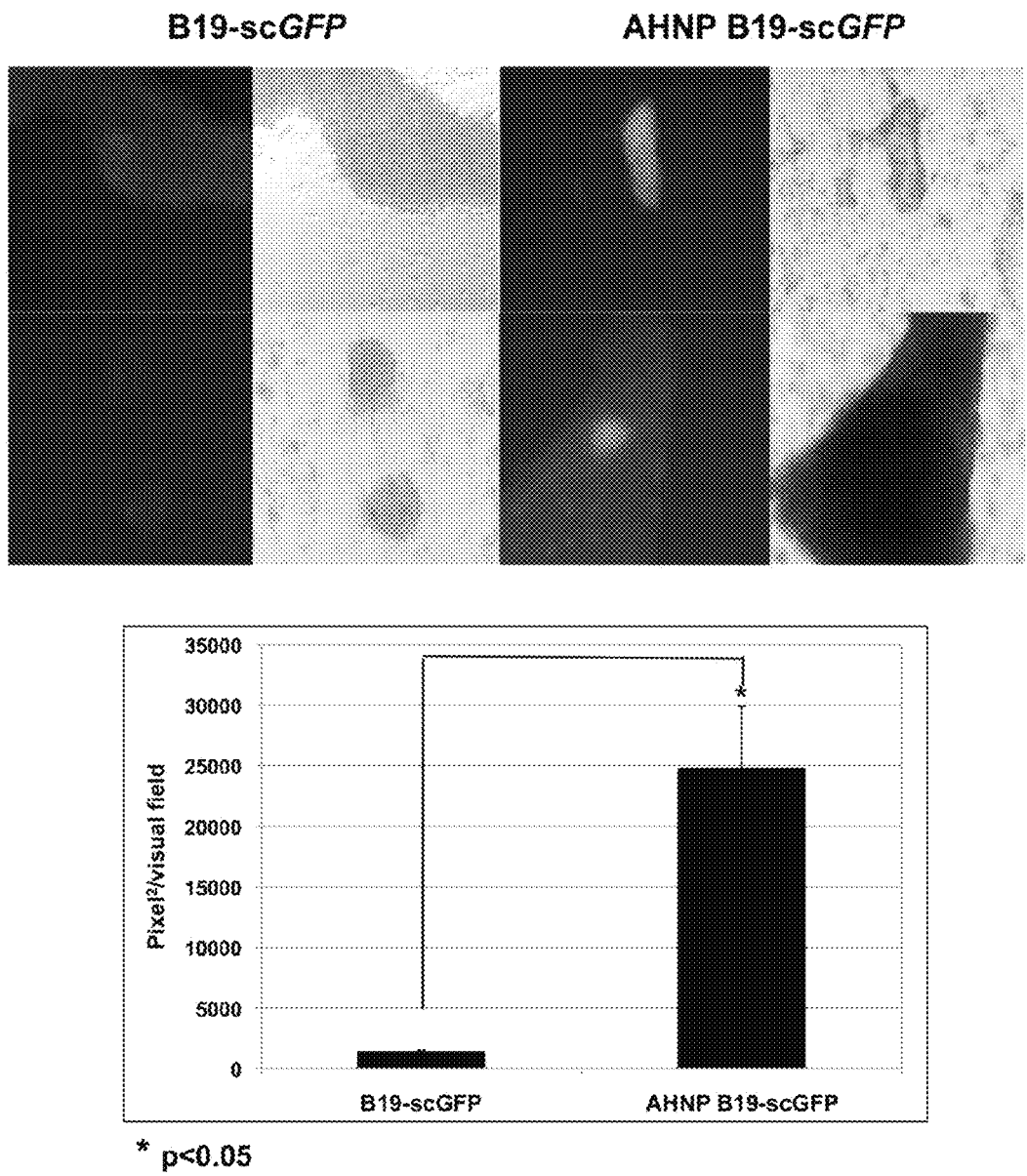

Murine MMTV-HER2/neu mammary tumor epithelial cells have a tendency to form small tumor nodules upon continued culture in vitro (FIG. 3, phase contrast microscopy images) and the efficiency of B19-scGFP and AHNP-B19-scGFP vectors to transduce MMTV-HER2/neu cells and nodules was evaluated. MMTV-HER2/neu cells were incubated with B19-scGFP and AHNP-B19-scGFP vectors at MOI 10 and cells observed under a fluorescent microscope 48 h after infection. Low levels of GFP-positive cells were detected in cells exposed to B19-scGFP virions (FIG. 3, top, columns on the left), suggesting the presence of P antigen receptors and β1 integrin co-receptors on these cells. We had previously observed low-level transduction of murine fibroblasts (55) and murine hematopoietic progenitor cells (Weigel-Van Aken K A unpublished observation) with B19-scGFP vectors, suggesting that murine P antigen (which could not be quantified due to unavailability of antibodies to murine P antigen) and murine β1 integrins (which are expressed abundantly on murine fibroblasts (55)) are functional receptors and co-receptors for B19-scGFP vector entry. When MMTV-HER2/neu cells were exposed to AHNP-B19-scGFP vectors, a ~10-fold increase in GFP transgene expression was observed (FIG. 3, bottom) and GFP-positive cells were observed in cells growing as monolayer and cells within tumor nodules (FIG. 3, top, columns on the right). These results documented enhanced vector targeting to HER2/neu-positive cells by incorporation of 60 copies of an anti-HER2 antibody mimic peptide (AHNP) into the B19 capsid.

Dependence of AHNP-B19-scGFP Vector Transduction on HER2 Receptor Activation.

It is well documented that HER2/neu receptors undergo endocytosis only after activation which involves (i) receptor homo- or hetero-dimerization with other members of the EGFR family; (ii) enhanced tyrosine kinase activity leading to HER2/neu autophosphorylation at cytoplasmic tyrosine residues (including Tyr-1248) and phosphorylation of other protein substrates (58). Phosphorylation of the cytoplasmic Tyr-1248, which is located within a NPXY internalization signal, has been demonstrated to be sufficient to trigger the internalization of dimerized HER2/neu via coated pits (22). In order to determine whether AHNP-B19-scGFP transduction required HER2/neu activation, peptides derived from the activation loop of the HER2/neu kinase domain (p1; 49) and from the transmembrane domain of the receptor (p2; 29) were used in inhibitor studies.

Figure 4A:
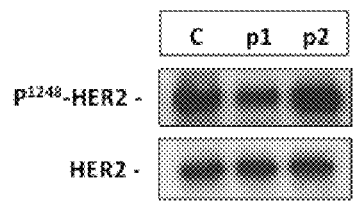

Reduced phosphorylation of Tyr-1248 was observed in MMTV-HER2/neu cells exposed to the HER2 kinase domain-derived peptide (p1), but not to the transmembrane domain-derived peptide (p2) (FIG. 4A). Transduction of MMTV-HER2/neu cells with AHNP-B19scGFP vectors was ~10-fold higher than transduction with B19-scGFP (FIG. 4C) and it was 90% reduced following exposure of the cells to the HER2 kinase domain-derived peptide (p1) (FIG. 4B, third panel on the right; FIG. 4C, AHNP+p1), suggesting that kinase activity of HER2/neu was required for AHNP-B19-scGFP entry. A 40% reduction in transduction efficiency was observed with the transmembrane domain-derived peptide (p2) (FIG. 4C, AHNP+p2). Transduction with AHNP-B19-scGFP vectors was integrin β1 coreceptor-dependent, as demonstrated by a ~96% inhibition following incubation with a function-blocking integrin β1 antibody (FIG. 4B, second panel on the right; FIG. 4C, AHNP+β1 Ab) that we demonstrated previously abrogates β1 integrin coreceptor function for B19 entry (53). As expected, preincubation of the virions with P antigen did not affect AHNP-B19-scGFP transduction (FIG. 4B, fourth panel on the right; FIG. 4C, AHNP+P Ag). This observation demonstrated that the chimeric B19 capsid was no longer able to bind P antigen and validates the previously mapped binding site.

Figure 4B:
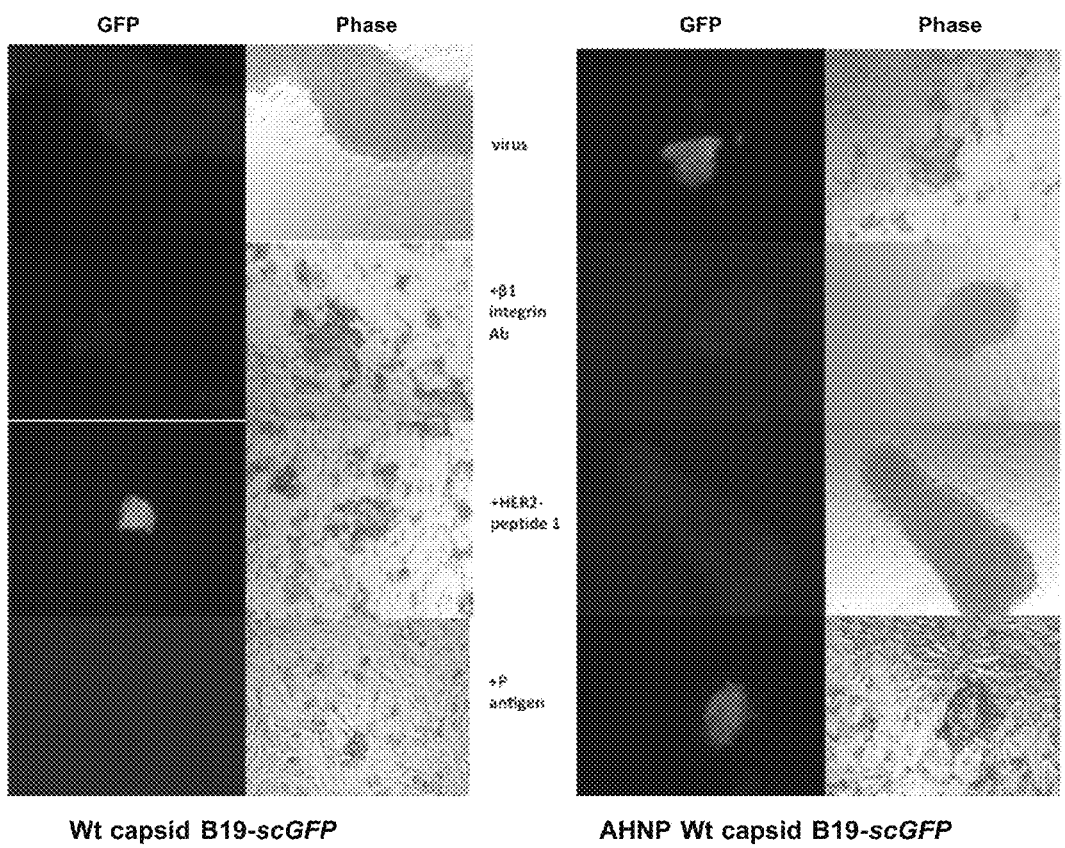
Figure 4C:
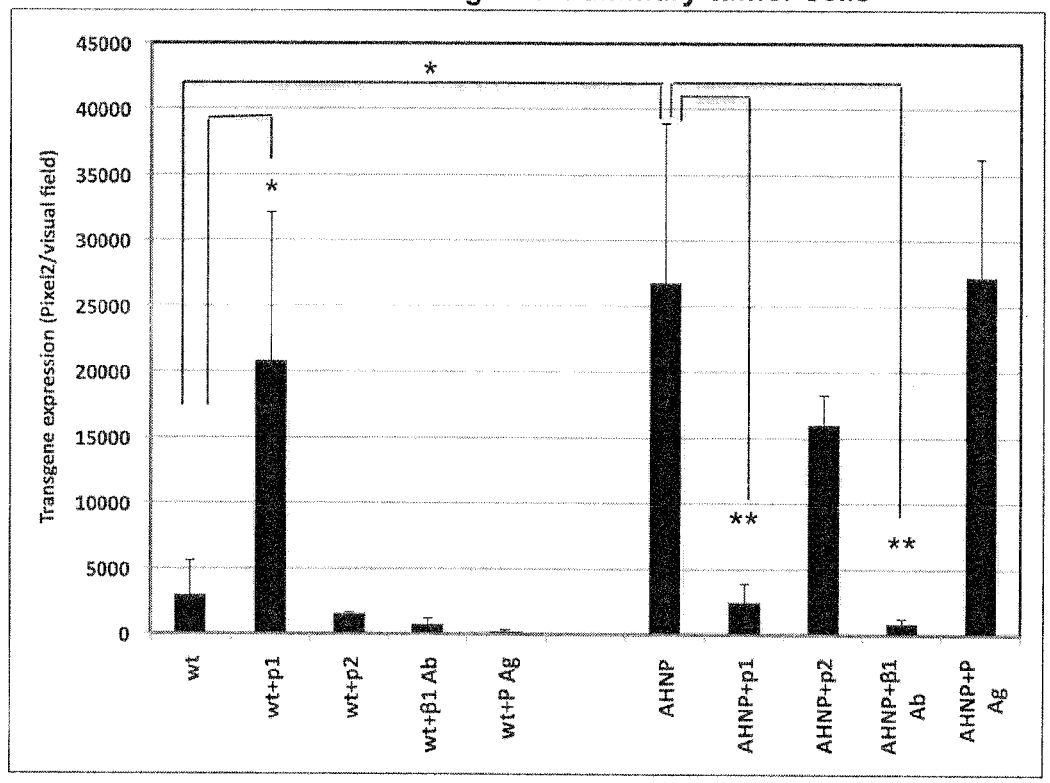

Somewhat surprising, transduction efficiency of B19-scGFP vectors was ~7-fold enhanced by exposure of MMTV-HER2/neu cells to the HER2 kinase domain-derived peptide (p1) (FIG. 4B, third panel on the left; FIG. 4C, wt+p1), and was ~73% and ~93% inhibited, as expected, by preincubation of the cells with a function-blocking integrin β1 antibody and pre-incubation of the virions with P antigen, respectively (FIG. 4B, second and fourth panels on the left, FIG. 4C, wt+β1 Ab, wt+P Ag). Taken together these results demonstrated that replacement of the P antigen binding epitope on B19 capsids by an AHNP peptide had successfully removed vector dependence on P antigen as primary receptor for binding to the cell surface and introduced binding to HER2/neu as receptor for AHNP-B19 vector entry. Importantly, HER2/neu-binding AHNP-B19 vectors still used β1 integrins as co-receptors for infection.

AHNP Vector Transduction of Medulloblastoma Cells.

Figure 5:
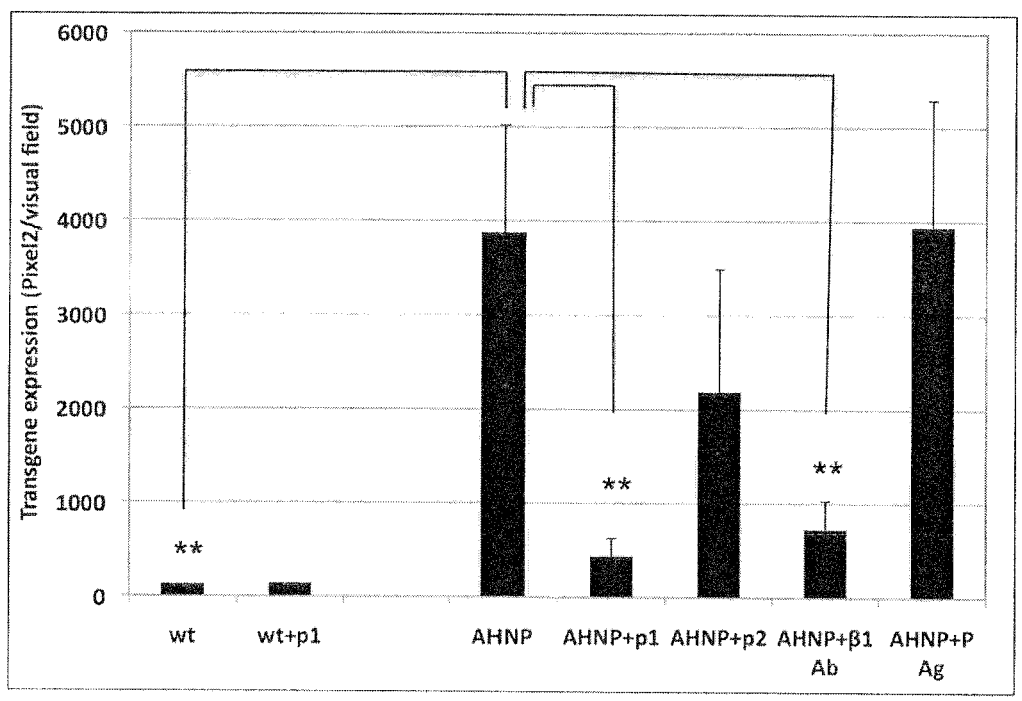

Expression levels of HER2/neu receptors on breast cancer cells and MMTV-HER2/neu transgenic murine tumor cells can reach 100-fold the levels on non-cancerous cells, frequently leading to receptor homo-dimerization and self-activation (2). It was therefore of interest whether AHNP-B19 vectors could transduce cells expressing lower levels of HER2/neu, precluding receptor homo-dimerization and self-activation. Human medulloblastoma cells (Daoy) overexpress HER2/neu in about 30-40% of tumors by ~5-fold, which is substantially lower than the up to 100-fold overexpression found on breast cancer cells (3) and are not sensitive to trastazumab treatment (3, 24). When Daoy cells were exposed to B19-scGFP and AHNP-B19-scGFP vectors, very low levels of GFP transgene expression were observed in B19-scGFP exposed and ~29-fold higher levels with AHNP-B19-scGFP (FIG. 5). Interestingly, incubation of Daoy cells with the HER2 kinase domain-derived peptide (p1) did not result in increased transduction with B19-scGFP vectors, as was observed in MMTV-HER2/neu murine breast tumor cells (FIG. 5, compare FIGS. 4B and 4C). Although the overall levels of transgene expression were lower in AHNP-B19-scGFP-transduced Daoy compared to MMTV-HER2/neu cells, transduction was also inhibited by pre-incubation of cells with either the HER2 kinase domain-derived peptide (p1) or the β1 integrin function-blocking antibody (FIG. 5). Preincubation of AHNP-B19-scGFP virions with P antigen, in contrast, had no effect on transduction efficiency (FIG. 5). These results corroborated that AHNP-B19-scGFP virions infected target cells through HER2/neu receptors and β1 integrins co-receptors. The results also documented that cells with lower expression levels of HER2/neu receptors that preclude receptor homodimerization and self-activation can be successfully targeted by AHNP-B19 vectors.

Discussion

Interaction of parvovirus B19 with P antigen has been mapped to a 6 amino acid peptide on the surface-exposed loop 4 of VP2 by cryo-electron microscopy (12). We provide support for this finding by replacing this peptide and demonstrating loss of competitive inhibition of B19 infection with P antigen. Although we could not directly measure the levels of P antigen on murine MMTV-HER2/neu transgenic breast tumor cells, the fact that B19-scGFP vectors could transduce these cells, especially when HER2/neu receptors were functionally silenced, provides evidence for the functionality of murine P antigen and murine β1 integrins for B19 transduction, and corroborates our previous observations of murine fibroblast and murine hematopoietic progenitor cell transduction by B19-scGFP vectors ((55) and unpublished observation).

The anti-HER2/neu peptide (AHNP) was chosen for insertion into B19 VP2, since antibodies to HER2/neu (Herceptin®/trastazumab) have been used successfully in clinical trials to target HER2/neu-positive breast cancer cells and short peptides derived from the complementarity-determining region (CDR-H3) of the HER2 antibody have demonstrated favorable HER2/neu binding affinity (8, 37). In addition, the CDR-H3-derived AHNP peptide could be structurally aligned with the B19 VP2 loop 4 in such a way that the HER2/neu-binding residues (DGFYA) were maximally exposed on the loop when replacing the P antigen-binding residues. Introduction of AHNP into B19 VP2 loop 4 significantly increased the transduction of murine HER2/neu-overexpressing (MMTV-HER2/neu) and human HER2/neu-expressing (Daoy) cells, retained dependence on β1 integrin coreceptors and restricted viral entry to cells expressing functionally active HER2/neu kinase receptors. These results corroborate the feasibility of changing the tropism of parvovirus B19 for P antigen-positive cells and retargeting B19 vectors to alternative cell surface receptors. The dependence of AHNP-B19 entry on both, activated HER2/neu kinases and activated β1 integrins, might have importance for the applicability of AHNP-B19 vectors, since cells with HER2/neu amplification overexpress HER2/neu receptors up to 100-fold above normal levels (11) and HER2/neu overexpression has been shown to lead to receptor homo-dimerization and self-activation (2), making these cells good targets for AHNP-B19 vectors. Normal cells, in contrast, express low levels of HER2/neu, lack homo-dimerization and receptor self-activation and are less likely targets. The dependence of AHNP-B19 transduction on functionally active β1 integrins will likely contribute to its feasibility to target HER2/neu-positive breast cancer metastases in the bone marrow, the occurrence of which has been documented in ~30% of breast cancer patients at diagnosis (9), since bone marrow-resident cancer cells use β1 integrins for survival under genotoxic stress conditions including irradiation and chemotherapy (14, 46) (15).

Intriguing was the observation that HER2/neu receptor kinase activity negatively affected B19-scGFP transduction, specifically of cells with high levels of HER2/neu overexpression and that inhibition of the HER2/neu kinase using a kinase domain-derived peptide significantly enhanced B19-scGFP transduction. Overexpression of HER2/neu in cultured cells has been demonstrated to lead to HER2/neu activation (16) and transfection of an inducible homo-dimerizing HER2-construct into non-malignant human mammary epithelial cells induced morphological changes characteristic of an epithelial-mesenchymal conversion and functional impairment of β1 integrins; an effect that could be reversed with β1 integrin activating antibodies (6) (27).

Although a HER2/neu-dependent suppression of β1 integrin function could have caused the low transduction of MMTV-HER2/neu cells with B19-scGFP, it did not prevent the efficient transduction with AHNP-B19 vectors, which was clearly β1 integrin coreceptor-dependent. Alternatively, a potential effect of constitutively activated HER2/neu on glycolipid receptors such as P antigen could be involved, especially since P antigen has been shown to be internalized through caveolae (41) and a negative reciprocal regulation between HER2/neu and caveolin-1 affecting caveolae-mediated internalization processes has been documented (19).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Adelsman, M. A., J. B. McCarthy, and Y. Shimizu. 1999. Stimulation of beta1-integrin function by epidermal growth factor and heregulin-beta has distinct requirements for erbB2 but a similar dependence on phosphoinositide 3-OH kinase. Mol Biol Cell 10:2861-78.
2. Agus, D. B., R. W. Akita, W. D. Fox, G. D. Lewis, B. Higgins, P. I. Pisacane, J. A. Lofgren, C. Tindell, D. P. Evans, K. Maiese, H. I. Scher, and M. X. Sliwkowski. 2002. Targeting ligand-activated ErbB2 signaling inhibits breast and prostate tumor growth. Cancer Cell 2:127-37.
3. Ahmed, N., M. Ratnayake, B. Savoldo, L. Perlaky, G. Dotti, W. S. Wels, M. B. Bhattacharjee, R. J. Gilbertson, H. D. Shine, H. L. Weiss, C. M. Rooney, H. E. Heslop, and S. Gottschalk. 2007. Regression of experimental medulloblastoma following transfer of HER2-specific T cells. Cancer Res 67:5957-64.
4. Amit, A. G., R. A. Mariuzza, S. E. Phillips, and R. J. Poljak. 1986. Three-dimensional structure of an antigen-antibody complex at 2.8 A resolution. Science 233:747-53.
5. Arnould, L., M. Gelly, F. Penault-Llorca, L. Benoit, F. Bonnetain, C. Migeon, V. Cabaret, V. Fermeaux, P. Bertheau, J. Garnier, J. F. Jeannin, and B. Coudert. 2006. Trastuzumab-based treatment of HER2-positive breast cancer: an antibody-dependent cellular cytotoxicity mechanism? Br J Cancer 94:259-67.
6. Baeckstrom, D., P. J. Lu, and J. Taylor-Papadimitriou. 2000. Activation of the alpha2beta1 integrin prevents c-erbB2-induced scattering and apoptosis of human mammary epithelial cells in collagen. Oncogene 19:4592-603.
7. Berezov, A., M. I. Greene, and R. Murali. 2003. Structure-based approaches to inhibition of erbB receptors with peptide mimetics. Immunol Res 27:303-8.
8. Berezov, A., H. T. Zhang, M. I. Greene, and R. Murali. 2001. Disabling erbB receptors with rationally designed exocyclic mimetics of antibodies: structure-function analysis. J Med Chem 44:2565-74.
9. Braun, S., F. D. Vogl, B. Naume, W. Janni, M. P. Osborne, R. C. Coombes, G. Schlimok, I. J. Diel, B. Gerber, G. Gebauer, J. Y. Pierga, C. Marth, D. Oruzio, G. Wiedswang, E. F. Solomayer, G. Kundt, B. Strobl, T. Fehm, G. Y. Wong, J. Bliss, A. Vincent-Salomon, and K. Pantel. 2005. A pooled analysis of bone marrow micrometastasis in breast cancer. N Engl J Med 353:793-802.
10. Brown, K. E., S. M. Anderson, and N. S. Young. 1993. Erythrocyte P antigen: cellular receptor for B19 parvovirus. Science 262:114-7.
11. Burstein, H. J. 2005. The distinctive nature of HER2-positive breast cancers. N Engl J Med 353:1652-4.
12. Chipman, P. R., M. Agbandje-McKenna, S. Kajigaya, K. E. Brown, N. S. Young, T. S. Baker, and M. G. Rossmann. 1996. Cryo-electron microscopy studies of empty capsids of human parvovirus B19 complexed with its cellular receptor. Proc Natl Acad Sci USA 93:7502-6.
13. Codony-Servat, J., J. Albanell, J. C. Lopez-Talavera, J. Arribas, and J. Baselga. 1999. Cleavage of the HER2 ectodomain is a pervanadate-activable process that is inhibited by the tissue inhibitor of metalloproteases-1 in breast cancer cells. Cancer Res 59:1196-201.
14. Cordes, N., B. Hansmeier, C. Beinke, V. Meineke, and D. van Beuningen. 2003. Irradiation differentially affects substratum-dependent survival, adhesion, and invasion of glioblastoma cell lines. Br J Cancer 89:2122-32.
15. Cordes, N., J. Seidler, R. Durzok, H. Geinitz, and C. Brakebusch. 2006. beta1-integrin-mediated signaling essentially contributes to cell survival after radiation-induced genotoxic injury. Oncogene 25:1378-90.
16. Di Fiore, P. P., J. H. Pierce, M. H. Kraus, O. Segatto, C. R. King, and S. A. Aaronson. 1987. erbB-2 is a potent oncogene when overexpressed in NIH/3T3 cells. Science 237:178-82.
17. Dowsett, M., M. Procter, W. McCaskill-Stevens, E. de Azambuja, U. Dafni, J. Rueschoff, B. Jordan, S. Dolci, M. Abramovitz, O. Stoss, G. Viale, R. D. Gelber, M. Piccart-Gebhart, and B. Leyland-Jones. 2009. Disease-free survival according to degree of HER2 amplification for patients treated with adjuvant chemotherapy with or without 1 year of trastuzumab: the HERA Trial. J Clin Oncol 27:2962-9.
18. Emsley, P., and K. Cowtan. 2004. Coot: model-building tools for molecular graphics. Acta Crystallogr D Biol Crystallogr 60:2126-32.
19. Engelman, J. A., R. J. Lee, A. Karnezis, D. J. Bearss, M. Webster, P. Siegel, W. J. Muller, J. J. Windle, R. G. Pestell, and M. P. Lisanti. 1998. Reciprocal regulation of neu tyrosine kinase activity and caveolin-1 protein expression in vitro and in vivo. Implications for human breast cancer. J Biol Chem 273:20448-55.
20. Falcioni, R., A. Antonini, P. Nistico, S. Di Stefano, M. Crescenzi, P. G. Natali, and A. Sacchi. 1997. Alpha 6 beta 4 and alpha 6 beta 1 integrins associate with ErbB-2 in human carcinoma cell lines. Exp Cell Res 236:76-85.
21. Fehm, T., V. Muller, B. Aktas, W. Janni, A. Schneeweiss, E. Stickeler, C. Lattrich, C. R. Lohberg, E. Solomayer, B. Rack, S. Riethdorf, C. Klein, C. Schindlbeck, K. Brocker, S. Kasimir-Bauer, D. Wallwiener, and K. Pantel. HER2 status of circulating tumor cells in patients with metastatic breast cancer: a prospective, multicenter trial. Breast Cancer Res Treat 124:403-12.
22. Gilboa, L., R. Ben-Levy, Y. Yarden, and Y. I. Henis. 1995. Roles for a cytoplasmic tyrosine and tyrosine kinase activity in the interactions of Neu receptors with coated pits. J Biol Chem 270:7061-7.
23. Harari, D., and Y. Yarden. 2000. Molecular mechanisms underlying ErbB2/HER2 action in breast cancer. Oncogene 19:6102-14.
24. Hernan, R., R. Fasheh, C. Calabrese, A. J. Frank, K. H. Maclean, D. Allard, R. Barraclough, and R. J. Gilbertson.

25. Joensuu, H., P. L. Kellokumpu-Lehtinen, P. Bono, T. Alanko, V. Kataja, R. Asola, T. Utriainen, R. Kokko, A. Hemminki, M. Tarkkanen, T. Turpeenniemi-Hujanen, S. Jyrkkio, M. Flander, E. Helle, S. Ingalsuo, K. Johansson, A. S. Jaaskelainen, M. Pajunen, M. Rauhala, J. Kaleva-Kerola, T. Salminen, M. Leinonen, I. Elomaa, and J. Isola. 2006, Adjuvant docetaxel or vinorelbine with or without trastuzumab for breast cancer. N Engl J Med 354:809-20.

26. Klapper, L. N., H. Waterman, M. Sela, and Y. Yarden. 2000. Tumor-inhibitory antibodies to HER-2/ErbB-2 may act by recruiting c-Cbl and enhancing ubiquitination of HER-2. Cancer Res 60:3384-8.

27. Lindberg, L. E., S. Hedjazifar, and D. Baeckstrom. 2002. c-erbB2-induced disruption of matrix adhesion and morphogenesis reveals a novel role for protein kinase B as a negative regulator of alpha(2)beta(1) integrin function. Mol Biol Cell 13:2894-908.

28. Masuda, K., M. Richter, X. Song, A. Berezov, R. Murali, M. I. Greene, and H. Zhang. 2006. AHNP-streptavidin: a tetrameric bacterially produced antibody surrogate fusion protein against p185her2/neu. Oncogene 25:7740-6.

29. Mittendorf, E. A., C. E. Storrer, R. J. Foley, K. Harris, Y. Jama, C. D. Shriver, S. Ponniah, and G. E. Peoples. 2006. Evaluation of the HER2/neu-derived peptide GP2 for use in a peptide-based breast cancer vaccine trial. Cancer 106:2309-17.

30. Molina, M. A., J. Codony-Servat, J. Albanell, F. Rojo, J. Arribas, and J. Baselga. 2001. Trastuzumab (herceptin), a humanized anti-Her2 receptor monoclonal antibody, inhibits basal and activated Her2 ectodomain cleavage in breast cancer cells. Cancer Res 61:4744-9.

31. Monferran, S., C. Muller, L. Mourey, P. Frit, and B. Salles. 2004. The Membrane-associated form of the DNA repair protein Ku is involved in cell adhesion to fibronectin. J Mol Biol 337:503-11.

32. Moro, L., M. Venturino, C. Bozzo, L. Silengo, F. Altruda, L. Beguinot, G. Tarone, and P. Defilippi. 1998. Integrins induce activation of EGF receptor: role in MAP kinase induction and adhesion-dependent cell survival. EMBO J 17:6622-32.

33. Muller, W. J., E. Sinn, P. K. Pattengale, R. Wallace, and P. Leder. 1988. Single-step induction of mammary adenocarcinoma in transgenic mice bearing the activated e-neu oncogene. Cell 54:105-15.

34. Munakata, Y., T. Saito-Ito, K. Kumura-Ishii, J. Huang, T. Kodera, T. Ishii, Y. Hirabayashi, Y. Koyanagi, and T. Sasaki. 2005. Ku80 autoantigen as a cellular coreceptor for human parvovirus B19 infection. Blood 106:3449-56.

35. Munzone, E., F. Nole, A. Goldhirsch, E. Botteri, A. Esposito, L. Zorzino, G. Curigliano, I. Minchella, L. Adamoli, M. C. Cassatella, C. Casadio, and M. T. Sandri. Changes of HER2 status in circulating tumor cells compared with the primary tumor during treatment for advanced breast cancer. Clin Breast Cancer 10:392-7.

36. Nishimura, R., Y. Okumura, and N. Arima. 2008. Trastuzumab monotherapy versus combination therapy for treating recurrent breast cancer: time to progression and survival. Breast Cancer 15:57-64.

37. Park, B. W., H. T. Zhang, C. Wu, A. Berezov, X. Zhang, R. Dua, Q. Wang, G. Kao, D. M. O'Rourke, M. I. Greene, and R. Murali. 2000. Rationally designed anti-HER2/neu peptide mimetic disables P185HER2/neu tyrosine kinases in vitro and in vivo. Nat Biotechnol 18:194-8.

38. Perez, E. A., M. M. Reinholz, D. W. Hillman, K. S. Tenner, M. J. Schroeder, N. E. Davidson, S. Martino, G. W. Sledge, L. N. Harris, J. R. Gralow, A. C. Dueck, R. P. Ketterling, J. N. Ingle, W. L. Lingle, P. A. Kaufman, D. W. Visscher, and R. B. Jenkins. HER2 and chromosome 17 effect on patient outcome in the N9831 adjuvant trastuzumab trial. J Clin Oncol 28:4307-15.

39. Pestrin, M., S. Bessi, F. Galardi, M. Truglia, A. Biggeri, C. Biagioni, S. Cappadona, L. Biganzoli, A. Giannini, and A. Di Leo. 2009. Correlation of HER2 status between primary tumors and corresponding circulating tumor cells in advanced breast cancer patients. Breast Cancer Res Treat 118:523-30.

40. Piccart-Gebhart, M. J., M. Procter, B. Leyland-Jones, A. Goldhirsch, M. Untch, I. Smith, L. Gianni, J. Baselga, R. Bell, C. Jackisch, D. Cameron, M. Dowsett, C. H. Barrios, G. Steger, C. S. Huang, M. Andersson, M. Inbar, M. Lichinitser, I. Lang, U. Nitz, H. Iwata, C. Thomssen, C. Lohrisch, T. M. Suter, J. Ruschoff, T. Suto, V. Greatorex, C. Ward, C. Straehle, E. McFadden, M. S. Dolci, and R. D. Gelber. 2005. Trastuzumab after adjuvant chemotherapy in HER2-positive breast cancer. N Engl J Med 353:1659-72.

41. Puri, V., R. Watanabe, R. D. Singh, M. Dominguez, J. C. Brown, C. L. Wheatley, D. L. Marks, and R. E. Pagano. 2001. Clathrin-dependent and -independent internalization of plasma membrane sphingolipids initiates two Golgi targeting pathways. J Cell Biol 154:535-47.

42. Romond, E. H., E. A. Perez, J. Bryant, V. J. Suman, C. E. Geyer, Jr., N. E. Davidson, E. Tan-Chiu, S. Martino, S. Paik, P. A. Kaufman, S. M. Swain, T. M. Pisansky, L. Fehrenbacher, L. A. Kutteh, V. G. Vogel, D. W. Visscher, G. Yothers, R. B. Jenkins, A. M. Brown, S. R. Dakhil, E. P. Mamounas, W. L. Lingle, P. M. Klein, J. N. Ingle, and N. Wolmark. 2005. Trastuzumab plus adjuvant chemotherapy for operable HER2-positive breast cancer. N Engl J Med 353:1673-84.

43. Saragovi, H. U., D. Fitzpatrick, A. Raktabutr, H. Nakanishi, M. Kahn, and M. I. Greene. 1991. Design and synthesis of a mimetic from an antibody complementarity-determining region. Science 253:792-5.

44. Schreiber, T. D., C. Steinl, M. Essl, H. Abele, K. Geiger, C. A. Muller, W. K. Aicher, and G. Klein. 2009. The integrin alpha9beta1 on hematopoietic stem and progenitor cells: involvement in cell adhesion, proliferation and differentiation. Haematologica 94:1493-501.

45. Schwede, T., J. Kopp, N. Guex, and M. C. Peitsch. 2003. SWISS-MODEL: An automated protein homology-modeling server. Nucleic Acids Res 31:3381-5.

46. Sethi, T., R. C. Rintoul, S. M. Moore, A. C. MacKinnon, D. Salter, C. Choo, E. R. Chilvers, I. Dransfield, S. C. Donnelly, R. Strieter, and C. Haslett. 1999. Extracellular matrix proteins protect small cell lung cancer cells against apoptosis: a mechanism for small cell lung cancer growth and drug resistance in vivo. Nat Med 5:662-8.

47. Slamon, D. J., G. M. Clark, S. G. Wong, W. J. Levin, A. Ullrich, and W. L. McGuire. 1987. Human breast cancer: correlation of relapse and survival with amplification of the HER-2/neu oncogene. Science 235:177-82.

48. Sliwkowski, M. X., J. A. Lofgren, G. D. Lewis, T. E. Hotaling, B. M. Fendly, and J. A. Fox. 1999. Nonclinical studies addressing the mechanism of action of trastuzumab (Herceptin). Semin Oncol 26:60-70.

49. Telesco, S. E., and R. Radhakrishnan. 2009. Atomistic insights into regulatory mechanisms of the HER2 tyrosine kinase domain: a molecular dynamics study. Biophys J 96:2321-34.

50. Vincent-Salomon, A., J. Y. Pierga, J. Couturier, C. D. d'Enghien, C. Nos, B. Sigal-Zafrani, M. Lae, P. Freneaux, V. Dieras, J. P. Thiery, and X. Sastre-Garau. 2007. HER2 status of bone marrow micrometastasis and their corresponding primary tumours in a pilot study of 27 cases: a possible tool for anti-HER2 therapy management? Br J Cancer 96:654-9.

51. Wang, F., V. M. Weaver, O. W. Petersen, C. A. Larabell, S. Dedhar, P. Briand, R. Lupu, and M. J. Bissell. 1998. Reciprocal interactions between beta1-integrin and epidermal growth factor receptor in three-dimensional basement membrane breast cultures: a different perspective in epithelial biology. Proc Natl Acad Sci USA 95:14821-6.

52. Wang. S. F., B. Xiang, R. Zent, V. Quaranta, A. Pozzi, and C. L. Arteaga. 2009. Transforming growth factor beta induces clustering of HER2 and integrins by activating Src-focal adhesion kinase and receptor association to the cytoskeleton. Cancer Res 69:475-82.

53. Weigel-Kelley, K. A., M. C. Yoder, and A. Srivastava. 2003. Alpha5beta1 integrin as a cellular coreceptor for human parvovirus B19: requirement of functional activation of beta1 integrin for viral entry. Blood 102:3927-33.

54. Weigel-Kelley, K. A., M. C. Yoder, and A. Srivastava. 2001. Recombinant human parvovirus B19 vectors: erythrocyte P antigen is necessary but not sufficient for successful transduction of human hematopoietic cells. J Virol 75:4110-6.

55. Weigel-Van Aken, K. A. 2009. Pharmacological activation of guanine nucleotide exchange factors for the small GTPase Rap1 recruits high-affinity beta1 integrins as coreceptors for parvovirus B19: improved ex vivo gene transfer to human erythroid progenitor cells. Hum Gene Ther 20:1665-78.

56. White, D. E., N. A. Kurpios, D. Zuo, J. A. Hassell, S. Blaess, U. Mueller, and W. J. Muller, 2004. Targeted disruption of beta1-integrin in a transgenic mouse model of human breast cancer reveals an essential role in mammary tumor induction. Cancer Cell 6:159-70.

57. Worthylake, R., L. K. Opresko, and H. S. Wiley. 1999. ErbB-2 amplification inhibits down-regulation and induces constitutive activation of both ErbB-2 and epidermal growth factor receptors. J Biol Chem 274:8865-74.

58. Yarden, Y. 1990. Agonistic antibodies stimulate the kinase encoded by the neu protooncogene in living cells but the oncogenic mutant is constitutively active. Proc Natl Acad Sci USA 87:2569-73.

59. Ricart, A. D. 2011. Antibody-drug conjugates of calicheamicin derivative: gemtuzumab ozogamicin and inotuzumab ozogamicin. Clin Cancer Res. 17: 6417-27.

60. van Rijt, S. H. et al. 2011. Functionalization of osmium arene anticancer complexes with (poly)arginine: effect on cellular uptake, internalization, and cytotoxicity. Bioconjugate Chem 22: 218-26.

61. Wang, S. et al. 2012. Novel Targeted System To Deliver Chemotherapeutic Drugs to EphA2-Expressing Cancer Cells. J Med Chem 55: 2427-36.

62. Kelly, R. D. et al, 2011. An antibody-cytotoxic conjugate, BIIB015, is a new targeted therapy for Cripto positive tumours. Europ J cancer 47: 1736-46.

63. Chau, Y. et al. 2006. Investigation of targeting mechanism of new dextran-peptide-methotrexate conjugates using biodistribution study in matrix-metalloproteinase-overexpressing tumor xenograft model. J Pharm Sci 95: 542-51.

64. Szabo, R. et al. 2010. Daunomycin-polypeptide conjugates with antitumor activity. Biochim Biophys Acta 1798: 2209-16.

65. Horan, T. C. et al. epub Aug. 2, 2011. Description of the cytotoxic effect of a novel drug Abietyl-Isothiocyanate on endometrial cancer cell lines. Invest New Drugs, pp. 1-11.

66. Wei, F. et al. 2012. Conjugation of paclitaxel on adeno-associated virus (AAV) nanoparticles for co-delivery of genes and drugs. Eur J Pharm Sci 46: 167-172.

67. Lockney, D. M. et al. 2011. The Red clover necrotic mosaic virus capsid as a multifunctional cell targeting plant viral nanoparticle. Bioconjugate Chem 22: 67-73.

---

We claim:

1. An isolated polypeptide in which the sequence YCDG-FYACYMDV (SEQ ID NO: 3) has been substituted into loop 4 of a parvovirus B19 VP2 capsid protein for the P antigen binding site, wherein loop 4 consists of residues 393 to 406 of SEQ ID NO: 1.

2. The isolated polypeptide according to claim 1, wherein said polypeptide comprises SEQ ID NO: 2.

3. A capsid comprising a polypeptide according to claim 1.

4. A parvovirus or hybrid parvovirus particle comprising a polypeptide according to claim 1.

5. A parvovirus or hybrid parvovirus vector comprising nucleic acid encoding one or more therapeutic agents or one or more reporter peptides or proteins or a therapeutic agent attached to or packaged inside a capsid, said parvovirus vector comprising a capsid comprising a polypeptide according to claim 1.

6. The parvovirus or hybrid parvovirus vector according to claim 5, wherein said one or more therapeutic agents is a suicide gene, a tumor suppressor gene or a gene encoding a cytokine.

7. The parvovirus or hybrid parvovirus vector according to claim 6, wherein said nucleic acid encodes one or more RNA molecules.

8. The parvovirus or hybrid parvovirus vector according to claim 5, wherein said one or more reporter peptides/proteins is Green Fluorescent Protein, β-galactosidase, alkaline phosphatase or chloramphenicol acetyltransferase.

9. A parvovirus or hybrid parvovirus vector comprising a cytotoxic compound or drug packaged, conjugated or infused in and/or associated with said parvovirus vector comprising a capsid comprising a polypeptide according to claim 1.

10. The parvovirus or hybrid parvovirus vector according to claim 5, wherein said vector comprises one or more therapeutic agents selected from the group consisting of DNA intercalators, taxanes, maytansine, methotrexate, anthracyclines and isothiocyanates attached to or packaged inside the capsid.

11. A pharmaceutical composition comprising a pharmaceutically-acceptable carrier, adjuvant or diluent and a polypeptide according to claim 1.

12. A method of delivering a nucleic acid, therapeutic agent, reporter protein/peptide or cytotoxic drug to a cell expressing one or more HER2/neu receptors comprising contacting said cell expressing one or more HER2/neu receptors with a parvovirus vector or a hybrid parvovirus vector according to claim 5, said parvovirus or hybrid parvovirus vector optionally being contained in a pharmaceutical composition.

13. The parvovirus or hybrid parvovirus vector according to claim 7, wherein said nucleic acid encodes one or more of the following: antisense RNA, siRNA, or shRNA and/or one or more of the following polypeptides: Herpes simplex virus thymidine kinase (HSV-tk), bacterial or fungal cytosine deaminase (CD), p53, p21WAF1/CIP1 (p21), pI6INK4a (p16), p18INK4c (p18), p27KIP2 (p27), Rb, Wt-1, NF1, VHL, APC, IL-1, IL-2, IL-4, IL-5, IL-12, IFN-α, IFN-β, IFN-γ, GM-CSF or TNF.

14. A pharmaceutical composition comprising a pharmaceutically-acceptable carrier, adjuvant or diluent and a parvovirus capsid according to claim 3.

15. A pharmaceutical composition comprising a pharmaceutically-acceptable carrier, adjuvant or diluent and a parvovirus or hybrid parvovirus particle according to claim 4.

16. A pharmaceutical composition comprising a pharmaceutically-acceptable carrier, adjuvant or diluent and a parvovirus or hybrid parvovirus vector according to claim 5.

* * * * *

UNITED STATES PATENT AND TRADEMARK OFFICE
CERTIFICATE OF CORRECTION

PATENT NO. : 9,598,468 B2  
APPLICATION NO. : 14/117871  
DATED : March 21, 2017  
INVENTOR(S) : Kirsten Ariane Kelley Weigel-Van Aken and Mavis Agbandje-McKenna Page 1 of 1

It is certified that error appears in the above-identified patent and that said Letters Patent is hereby corrected as shown below:

On the Title Page

(57) Abstract,
Line 15, "invention a" should read --invention are--.

In the Specification

Column 1,
Line 6, "APPLICATION APPLICATIONS" should read --APPLICATIONS--.

Column 8,
Line 29, "IFN-β, GM-CSF" should read --IFN-β, IFN-γ, GM-CSF--.

Column 10,
Line 6, "gift from." should read --gift from--.

Column 17,
Line 47, "activated e-neu" should read --activated c-neu--.

In the Claims

Column 28,
Line 60, "IFN-y," should read --IFN-γ,--.

Signed and Sealed this  
Seventeenth Day of October, 2017

Joseph Matal  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 7

<210> SEQ ID NO 1
<211> LENGTH: 554
<212> TYPE: PRT
<213> ORGANISM: Human parvovirus B19

<400> SEQUENCE: 1

Met Thr Ser Val Asn Ser Ala Glu Ala Ser Thr Gly Ala Gly Gly Gly
1               5                   10                  15

Gly Ser Asn Ser Val Lys Ser Met Trp Ser Glu Gly Ala Thr Phe Ser
            20                  25                  30

Ala Asn Ser Val Thr Cys Thr Phe Ser Arg Gln Phe Leu Ile Pro Tyr
        35                  40                  45

Asp Pro Glu His His Tyr Lys Val Phe Ser Pro Ala Ala Ser Ser Cys
    50                  55                  60

His Asn Ala Ser Gly Lys Glu Ala Lys Val Cys Thr Ile Ser Pro Ile
65                  70                  75                  80

Met Gly Tyr Ser Thr Pro Trp Arg Tyr Leu Asp Phe Asn Ala Leu Asn
                85                  90                  95

Leu Phe Phe Ser Pro Leu Glu Phe Gln His Leu Ile Glu Asn Tyr Gly
            100                 105                 110
```

-continued

```
Ser Ile Ala Pro Asp Ala Leu Thr Val Thr Ile Ser Glu Ile Ala Val
        115                 120                 125
Lys Asp Val Thr Asp Lys Thr Gly Gly Val Gln Val Thr Asp Ser
130                 135                 140
Thr Thr Gly Arg Leu Cys Met Leu Val Asp His Glu Tyr Lys Tyr Pro
145                 150                 155                 160
Tyr Val Leu Gly Gln Gly Gln Asp Thr Leu Ala Pro Glu Leu Pro Ile
                165                 170                 175
Trp Val Tyr Phe Pro Pro Gln Tyr Ala Tyr Leu Thr Val Gly Asp Val
                180                 185                 190
Asn Thr Gln Gly Ile Ser Gly Asp Ser Lys Lys Leu Ala Ser Glu Glu
                195                 200                 205
Ser Ala Phe Tyr Val Leu Glu His Ser Ser Phe Gln Leu Leu Gly Thr
        210                 215                 220
Gly Gly Thr Ala Thr Met Ser Tyr Lys Phe Pro Pro Val Pro Pro Glu
225                 230                 235                 240
Asn Leu Glu Gly Cys Ser Gln His Phe Tyr Glu Met Tyr Asn Pro Leu
                245                 250                 255
Tyr Gly Ser Arg Leu Gly Val Pro Asp Thr Leu Gly Gly Asp Pro Lys
                260                 265                 270
Phe Arg Ser Leu Thr His Glu Asp His Ala Ile Gln Pro Gln Asn Phe
        275                 280                 285
Met Pro Gly Pro Leu Val Asn Ser Val Ser Thr Lys Glu Gly Asp Ser
        290                 295                 300
Ser Ser Thr Gly Ala Gly Lys Ala Leu Thr Gly Leu Ser Thr Gly Thr
305                 310                 315                 320
Ser Gln Asn Thr Arg Ile Ser Leu Arg Pro Gly Pro Val Ser Gln Pro
                325                 330                 335
Tyr His His Trp Asp Thr Asp Lys Tyr Val Thr Gly Ile Asn Ala Ile
                340                 345                 350
Ser His Gly Gln Thr Thr Tyr Gly Asn Ala Glu Asp Lys Glu Tyr Gln
        355                 360                 365
Gln Gly Val Gly Arg Phe Pro Asn Glu Lys Glu Gln Leu Lys Gln Leu
        370                 375                 380
Gln Gly Leu Asn Met His Thr Tyr Phe Pro Asn Lys Gly Thr Gln Gln
385                 390                 395                 400
Tyr Thr Asp Gln Ile Glu Arg Pro Leu Met Val Gly Ser Val Trp Asn
                405                 410                 415
Arg Arg Ala Leu His Tyr Glu Ser Gln Leu Trp Ser Lys Ile Pro Asn
                420                 425                 430
Leu Asp Asp Ser Phe Lys Thr Gln Phe Ala Ala Leu Gly Gly Trp Gly
                435                 440                 445
Leu His Gln Pro Pro Gln Ile Phe Leu Lys Ile Leu Pro Pro Ser
        450                 455                 460
Gly Pro Ile Gly Gly Ile Lys Ser Met Gly Ile Thr Thr Leu Val Gln
465                 470                 475                 480
Tyr Ala Val Gly Ile Met Thr Val Thr Met Thr Phe Lys Leu Gly Pro
                485                 490                 495
Arg Lys Ala Thr Gly Arg Trp Asn Pro Gln Pro Gly Val Tyr Pro Pro
                500                 505                 510
His Ala Ala Gly His Leu Pro Tyr Val Leu Tyr Asp Pro Thr Ala Thr
        515                 520                 525
```

Asp Ala Lys Gln His His Arg His Gly Tyr Glu Lys Pro Glu Glu Leu
530                 535                 540

Trp Thr Ala Lys Ser Arg Val His Pro Leu
545 550

<210> SEQ ID NO 2
<211> LENGTH: 552
<212> TYPE: PRT
<213> ORGANISM: Artificial Sequence
<220> FEATURE:
<223> OTHER INFORMATION: Parvovirus B19 Chimeric VP2 Capsid Protein

<400> SEQUENCE: 2

Met Thr Ser Val Asn Ser Ala Glu Ala Ser Thr Gly Ala Gly Gly Gly
1 5 10 15

Gly Ser Asn Ser Val Lys Ser Met Trp Ser Glu Gly Ala Thr Phe Ser
20 25 30

Ala Asn Ser Val Thr Cys Thr Phe Ser Arg Gln Phe Leu Ile Pro Tyr
35 40 45

Asp Pro Glu His His Tyr Lys Val Phe Ser Pro Ala Ala Ser Ser Cys
50 55 60

His Asn Ala Ser Gly Lys Glu Ala Lys Val Cys Thr Ile Ser Pro Ile
65 70 75 80

Met Gly Tyr Ser Thr Pro Trp Arg Tyr Leu Asp Phe Asn Ala Leu Asn
85 90 95

Leu Phe Phe Ser Pro Leu Glu Phe Gln His Leu Ile Glu Asn Tyr Gly
100 105 110

Ser Ile Ala Pro Asp Ala Leu Thr Val Thr Ile Ser Glu Ile Ala Val
115 120 125

Lys Asp Val Thr Asp Lys Thr Gly Gly Gly Val Gln Val Thr Asp Ser
130 135 140

Thr Thr Gly Arg Leu Cys Met Leu Val Asp His Glu Tyr Lys Tyr Pro
145 150 155 160

Tyr Val Leu Gly Gln Gly Gln Asp Thr Leu Ala Pro Glu Leu Pro Ile
165 170 175

Trp Val Tyr Phe Pro Pro Gln Tyr Ala Tyr Leu Thr Val Gly Asp Val
180 185 190

Asn Thr Gln Gly Ile Ser Gly Asp Ser Lys Lys Leu Ala Ser Glu Glu
195 200 205

Ser Ala Phe Tyr Val Leu Glu His Ser Ser Phe Gln Leu Leu Gly Thr
210 215 220

Gly Gly Thr Ala Thr Met Ser Tyr Lys Phe Pro Pro Val Pro Pro Glu
225 230 235 240

Asn Leu Glu Gly Cys Ser Gln His Phe Tyr Glu Met Tyr Asn Pro Leu
245 250 255

Tyr Gly Ser Arg Leu Gly Val Pro Asp Thr Leu Gly Gly Asp Pro Lys
260 265 270

Phe Arg Ser Leu Thr His Glu Asp His Ala Ile Gln Pro Gln Asn Phe
275 280 285

Met Pro Gly Pro Leu Val Asn Ser Val Ser Thr Lys Glu Gly Asp Ser
290 295 300

Ser Ser Thr Gly Ala Gly Lys Ala Leu Thr Gly Leu Ser Thr Gly Thr
305 310 315 320

Ser Gln Asn Thr Arg Ile Ser Leu Arg Pro Gly Pro Val Ser Gln Pro
325 330 335

Tyr His His Trp Asp Thr Asp Lys Tyr Val Thr Gly Ile Asn Ala Ile
            340                 345                 350

Ser His Gly Gln Thr Thr Tyr Gly Asn Ala Glu Asp Lys Glu Tyr Gln
        355                 360                 365

Gln Gly Val Gly Arg Phe Pro Asn Glu Lys Glu Gln Leu Lys Gln Leu
    370                 375                 380

Gln Gly Leu Asn Met His Thr Tyr Tyr Cys Asp Gly Phe Tyr Ala Cys
385                 390                 395                 400

Tyr Met Asp Val Arg Pro Leu Met Val Gly Ser Val Trp Asn Arg Arg
                405                 410                 415

Ala Leu His Tyr Glu Ser Gln Leu Trp Ser Lys Ile Pro Asn Leu Asp
            420                 425                 430

Asp Ser Phe Lys Thr Gln Phe Ala Ala Leu Gly Gly Trp Gly Leu His
        435                 440                 445

Gln Pro Pro Pro Gln Ile Phe Leu Lys Ile Leu Pro Pro Ser Gly Pro
    450                 455                 460

Ile Gly Gly Ile Lys Ser Met Gly Ile Thr Thr Leu Val Gln Tyr Ala
465                 470                 475                 480

Val Gly Ile Met Thr Val Thr Met Thr Phe Lys Leu Gly Pro Arg Lys
                485                 490                 495

Ala Thr Gly Arg Trp Asn Pro Gln Pro Gly Val Tyr Pro Pro His Ala
            500                 505                 510

Ala Gly His Leu Pro Tyr Val Leu Tyr Asp Pro Thr Ala Thr Asp Ala
        515                 520                 525

Lys Gln His His Arg His Gly Tyr Glu Lys Pro Glu Glu Leu Trp Thr
    530                 535                 540

Ala Lys Ser Arg Val His Pro Leu
545                 550

<210> SEQ ID NO 3
<211> LENGTH: 12
<212> TYPE: PRT
<213> ORGANISM: Artificial Sequence
<220> FEATURE:
<223> OTHER INFORMATION: AHNP peptide

<400> SEQUENCE: 3

Tyr Cys Asp Gly Phe Tyr Ala Cys Tyr Met Asp Val
1               5                   10

<210> SEQ ID NO 4
<211> LENGTH: 12
<212> TYPE: PRT
<213> ORGANISM: Artificial Sequence
<220> FEATURE:
<223> OTHER INFORMATION: anti-HER2/neu antibody rhu 4D5 CDR-H3 loop
      amino acids

<400> SEQUENCE: 4

Arg Trp Gly Gly Asp Gly Phe Tyr Ala Met Asp Val
1               5                   10

<210> SEQ ID NO 5
<211> LENGTH: 14
<212> TYPE: PRT
<213> ORGANISM: Artificial Sequence
<220> FEATURE:
<223> OTHER INFORMATION: WtB19 sequence replaced by AHNP peptide
<220> FEATURE:
<221> NAME/KEY: MISC_FEATURE -continued

```
<223> OTHER INFORMATION: VP2 loop residues

<400> SEQUENCE: 5

Phe Pro Asn Lys Gly Thr Gln Gln Tyr Thr Asp Gln Ile Glu
1               5                   10

<210> SEQ ID NO 6
<211> LENGTH: 8
<212> TYPE: PRT
<213> ORGANISM: Artificial Sequence
<220> FEATURE:
<223> OTHER INFORMATION: WtB19 sequence replaced by AHNP peptide
<220> FEATURE:
<221> NAME/KEY: MISC_FEATURE
<222> LOCATION: (399)..(406)
<223> OTHER INFORMATION: P-antigen binding site footprint

<400> SEQUENCE: 6

Gln Gln Tyr Thr Asp Gln Ile Glu
1               5

<210> SEQ ID NO 7
<211> LENGTH: 5
<212> TYPE: PRT
<213> ORGANISM: Artificial Sequence
<220> FEATURE:
<223> OTHER INFORMATION: fragment of AHNP peptide

<400> SEQUENCE: 7

Asp Gly Phe Tyr Ala
1               5
```